United States Patent
Lippard et al.

(10) Patent No.: US 7,494,821 B2
(45) Date of Patent: Feb. 24, 2009

(54) FLUORESCEIN BASED SENSORS FOR TRACKING NITRIC OXIDE IN LIVE CELLS

(75) Inventors: Stephen J. Lippard, Cambridge, MA (US); Mi Hee Lim, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 255 days.

(21) Appl. No.: 11/498,280

(22) Filed: Aug. 1, 2006

(65) Prior Publication Data

US 2009/0017552 A1   Jan. 15, 2009

Related U.S. Application Data

(60) Provisional application No. 60/704,511, filed on Aug. 1, 2005.

(51) Int. Cl.
  *G01N 21/76*  (2006.01)
  *G01N 33/20*  (2006.01)
  *C07D 311/82* (2006.01)
  *C12Q 1/68*   (2006.01)

(52) U.S. Cl. .................. 436/172; 436/74; 549/223; 435/6

(58) Field of Classification Search ............ 436/172, 436/74; 549/223; 435/6
See application file for complete search history.

(56) References Cited

U.S. PATENT DOCUMENTS

| 6,121,452 A * | 9/2000 | Kalz et al. ............... 546/154 |
| 6,399,392 B1 * | 6/2002 | Haugland et al. ........... 436/172 |
| 2002/0146726 A1 * | 10/2002 | Matray et al. ................ 435/6 |
| 2004/0224420 A1 * | 11/2004 | Lippard et al. .............. 436/74 |

OTHER PUBLICATIONS

Burdette et al., ZP4, an Improved Neuronal Zn2+ Sensor of the Zinpyr Family, 2003, Journal of the American Chemical Society v. 125, p. 1778-1787.*
Nolan et al., Synthesis and Characterization of Zinc Sensors Based on a Monosubstituted Fluorescein Platform, 2004, Inorganic Chemistry, vol. 43, p. 2624-2635.*

* cited by examiner

*Primary Examiner*—Jill Warden
*Assistant Examiner*—Lore Ramillano
(74) *Attorney, Agent, or Firm*—Dana M. Gordon; Foley Hoag LLP

(57) ABSTRACT

The present invention is directed, in part, to coordination complexes for detecting analytes, and methods of making and using the same.

20 Claims, 9 Drawing Sheets $FL_n$ n = 1, R = $CO_2CH_3$
n = 2, R = $CO_2H$
n = 3, R = $CH_2OH$
n = 4, R = H
n = 5, R = $CH_3$ FL$_n$ n = 1, R = CO$_2$CH$_3$
n = 2, R = CO$_2$H
n = 3, R = CH$_2$OH
n = 4, R = H
n = 5, R = CH$_3$ CuCl$_2$ (1 μM)  +  Fluorescein-based ligand (1 μM)

| | + excess NO (g) | Time (F$_{max}$, min) |
|---|---|---|
| Cu(FL$_1$) | 2.5-fold | 60 |
| Cu(FL$_2$) | 8.3-fold | 70 |
| Cu(FL$_3$) | 3.4-fold | 15 |
| Cu(FL$_4$) | 31-fold | 20 |
| Cu(FL$_5$) | 16-fold | 5 |

US 7,494,821 B2

FLUORESCEIN BASED SENSORS FOR TRACKING NITRIC OXIDE IN LIVE CELLS

CROSS-REFERENCE TO RELATED APPLICATIONS

This application claims the benefit of U.S. Provisional Application No. 60/704,511, filed Aug. 1, 2005, the contents of which are hereby incorporated by this reference in their entirety.

GOVERNMENT SUPPORT

The invention was made with government support awarded by the National Science Foundation under NSF Grant No. CHE-0234951. Accordingly, the U.S. Government has certain rights in this invention.

INTRODUCTION

I. Fluorescent Sensors

Fluorescence technology has revolutionized cell biology and many areas of biochemistry. In certain instances, fluorescent molecules may be used to trace molecular and physiological events in living cells. Certain sensitive and quantitative fluorescence detection devices have made fluorescence measurements an ideal readout for in vitro biochemical assays. In addition some fluorescence measurement systems may be useful for determining the presence of analytes in environmental samples. Finally, because certain fluorescence detection systems are rapid and reproducible, fluorescence measurements are often critical for many high-throughput screening applications.

The feasibility of using fluorescence technology for a particular application is often limited by the availability of an appropriate fluorescent sensor. There are a number of features that are desirable in fluorescent sensors, some of which may or may not be present in any particular sensor. First, fluorescent sensors should produce a perceptible change in fluorescence upon binding a desired analyte. Second, fluorescent sensors should selectively bind a particular analyte. Third, to allow concentration changes to be monitored, fluorescent sensors should have a $K_d$ near the median concentration of the species under investigation. Fourth, fluorescent sensors, especially when used intracellularly, should produce a signal with a high brightness, the product of the quantum yield and extinction coefficient. Fifth, the wavelengths of both the light used to excite the fluorescent molecule (excitation wavelengths) and of the emitted light (emission wavelengths) are often important. If possible, for intracellular use, a fluorescent sensor should have excitation wavelengths exceeding 340 nm to permit use with glass microscope objectives and prevent UV-induced cell damage, and have emission wavelengths approaching 500 nm to avoid autofluorescence from native substances in the cell and allow use with typical fluorescence microscopy optical filter sets. Excitation and emission at even longer wavelengths, approaching the near-IR, are also of value. Sixth, ideal sensors should allow for passive and irreversible loading into cells. Finally, ideal sensors should exhibit increased fluorescence with increasing levels of analyte.

II. Nitric Oxide in Biological Systems

Since the discovery in the 1980s that nitric oxide (NO) is the endothelium-derived relaxing factor (EDRF), postulated biological roles for NO have continued to proliferate. For example, in addition to cardiovascular signaling, NO also seems to function as a neurotransmitter that may be important in memory and as a weapon to fight infection when released by immune system macrophages. Uncovering these roles and deciphering their implications is complicated by the array of reactions that this gaseous molecule undergoes. In a biological environment, NO can react with a host of targets, including dioxygen, oxygen radicals, thiols, amines and transition metal ions. Some of the products formed, such as $NO_2$ and $NO^+$, are pathophysiological agents, whereas others, such as S-nitrosothiols, may in fact themselves be NO-transfer agents. Transition metal centers, especially iron in oxyhemoglobin, can rapidly scavenge free NO, thereby altering the amount available for signaling purposes.

The concentration-dependent lifetime of NO as well as its ability to diffuse freely through cellular membranes further complicate the delineation of these various processes. With a lifetime of up to 10 min under some conditions and a diffusion range of 100-200 μm, the biological action of NO can be distant from its point of origin. A diffusional spread of 200 μm corresponds to a volume containing approximately 2 million synapses.

A variety of analytical methods are available to monitor aspects of NO in biology, each having certain limitations. The Griess assay, for instance, is useful for estimating total NO production, but it is not very sensitive, cannot give real-time information and only measures the stable oxidation product nitrite. Although more sensitive and selective for NO, the chemiluminescent gas phase reaction of NO with ozone requires purging aqueous samples with an inert gas to strip NO into an analyzer. It too is therefore incapable of monitoring intracellular NO. Electrochemical sensing using microsensors provides in situ real-time detection of NO; the only spatial information obtained, however, is directly at the electrode tip and is therefore influenced by the placement of the probe.

Fluorescent NO sensors include DAF (diaminofluorescein) and DAN (2,3-diaminonaphthalene), the aromatic vicinal diamines of which react with nitrosating agents ($NO^+$ or $NO_2$) to afford fluorescent triazole compounds. DAF compounds can report intracellular NO, but their sensing ability relies on NO autoxidation products and not direct detection. A rhodamine-type fluorescent NO indicator similarly senses autoxidation products.

Fluorescent nitric oxide cheletropic traps (FNOCTs) are fluorescent versions of molecules that have been used as EPR spin probes and do react directly with NO. The initially formed nitroxide radical species formed are not fluorescent, however. Addition of a common biological reductant such as ascorbic acid is required to reduce the nitroxide and display increased fluorescence intensity.

However, existing imaging agents are not capable of direct, immediate, and selective NO detection, three highly desirable properties.

SUMMARY OF THE INVENTION

In one aspect, the present invention is directed to fluorescein-based sensors, and methods of making and using the same. Such sensors may be used to detect the presence of analytes, particularly nitric oxide (NO), in a direct, immediate and selective fashion.

The subject compositions, and methods of making and using the same, may achieve a number of desirable results and features, one or more of which (if any) may be present in any particular embodiment of the present invention: (i) the subject fluorescein-based compounds bind, optionally reversibly, a transition metal and desired analyte with a concomitant change in the fluorescence properties; (ii) a general schematic whereby a variety of useful sensors, varying optionally in the metal ion or fluorescein-based compound, may be constructed for use in detecting certain analytes; (iii) the subject sensors selectively bind certain analytes, optionally reversibly; (iv) sensors exhibit an increase in brightness (as opposed to a decrease) upon coordination of an analyte of interest; and (v) sensors may be capable of in vivo and other diagnostic use.

Further objectives and advantages of the present invention will become apparent as the description proceeds. To gain a full appreciation of the scope of the present invention, it will be further recognized that various aspects of the present invention can be combined to make desirable embodiments of the invention.

DETAILED DESCRIPTION OF THE INVENTION

Figure 1:
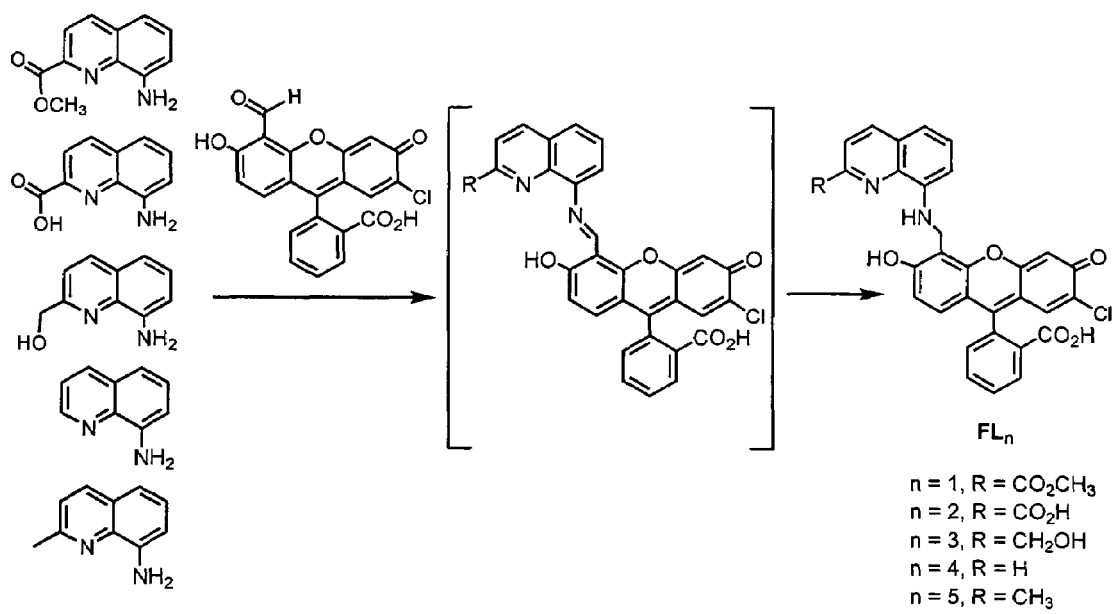
FIG. 1 depicts the synthetic strategies for five fluorescein ligands $FL_n$, (n=1-5).

Provided are sensors that are coordination complexes and may be used to detect certain analytes using fluorescence. In certain embodiments, there is a positive change in fluorescence upon exposure of an analyte of interest to a subject composition. Without limiting the invention to a particular mechanism of action or otherwise circumscribing the scope of the teachings herein, it is believed that the sensors detect NO via the redox chemistry of their transition metal components with NO. For example, in certain embodiments, the initial fluorescence of the sensor may be quenched in the presence of a paramagnetic copper (II) complex. Upon addition of NO, the copper (II) center is reduced to the diamagnetic copper(I) with closed d-shells, resulting in an increase in fluorescence.

I. DEFINITIONS

For convenience, before further description of the present invention, certain terms employed in the specification, examples and appended claims are collected here. These definitions should be read in light of the remainder of the disclosure and understood as by a person of ordinary skill in the art. Unless defined otherwise, all technical and scientific terms used herein have the same meaning as commonly understood by a person of ordinary skill in the art.

The articles "a" and "an" are used herein to refer to one or to more than one (i.e., to at least one) of the grammatical object of the article. By way of example, "an element" means one element or more than one element.

The terms "comprise" and "comprising" are used in the inclusive, open sense, meaning that additional elements may be included.

The term "including" is used herein to mean "including but not limited to". "Including" and "including but not limited to" are used interchangeably.

The term "fluorophore" is art-recognized and refers to a molecule or moiety, generally a polyaromatic hydrocarbon or heterocycle, that has the ability to fluoresce. The ability to fluoresce, or "fluorescence", of a fluorophore is generally understood to result from a three-stage process: (i) excitation, in which a photon is absorbed by the fluorophore, creating an excited electronic state in which the fluorophore has greater energy relative to the normal electronic state of the fluorophore; (ii) excited state lifetime, during which the fluorophore remains in the excited electronic state but also during which the energy of the state is partially dissipated; and (iii) emission, in which a photon of lower energy is emitted. Thus, a fluorophore absorbs a different wavelength of light (the "excitation wavelength") than it emits (the "emission wavelength"). Examples of fluorophores are described in more detail below. The terms "excitation wavelength" and "emission wavelength" are well-known in the art. The term "quantum yield" is art-recognized and refers to the efficiency of photon emission by the fluorophore and is described in more detail below.

The terms "Lewis base" and "Lewis basic" are art-recognized and generally include a chemical moiety, a structural fragment or substituent capable of donating a pair of electrons under certain conditions. It may be possible to characterize a Lewis base as donating a single electron in certain complexes, depending on the identity of the Lewis base and the metal ion, but for most purposes, however, a Lewis base is best understood as a two electron donor. Examples of Lewis basic moieties include uncharged compounds such as alcohols, thiols, and amines, and charged moieties such as alkoxides, thiolates, carbanions, and a variety of other organic anions. A Lewis base, when coordinated to a metal ion, is often referred to as a ligand. Further description of ligands relevant to the present invention is presented below.

The term "ligand" is art-recognized and refers to a species that interacts in some fashion with another species. In one example, a ligand may be a Lewis base that is capable of forming a coordinate bond with a Lewis acid. In other examples, a ligand is a species, often organic, that forms a coordinate bond with a metal ion. Ligands, when coordinated to a metal ion, may have a variety of binding modes know to those of skill in the art, which include, for example, terminal (i.e., bound to a single metal ion) and bridging (i.e., one atom of the Lewis base bound to more than one metal ion).

The terms "Lewis acid" and "Lewis acidic" are art-recognized and refer to chemical moieties which can accept a pair of electrons from a Lewis base as defined above.

The term "chelating agent" is art-recognized and refers to a molecule, often an organic one, and often a Lewis base, having two or more unshared electron pairs available for donation to a metal ion. The metal ion is usually coordinated by two or more electron pairs to the chelating agent. The terms, "bidentate chelating agent", "tridentate chelating agent", and "tetradentate chelating agent" refer to chelating agents having, respectively, two, three, and four electron pairs readily available for simultaneous donation to a metal ion coordinated by the chelating agent. Usually, the electron pairs of a chelating agent form coordinate bonds with a single metal ion; however, in certain examples, a chelating agent may form coordinate bonds with more than one metal ion, with a variety of binding modes being possible.

The term "coordination" is art-recognized and refers to an interaction in which one multi-electron pair donor coordinatively bonds (is "coordinated") to one metal ion.

The terms "coordinate bond" or "coordination bond" are art-recognized and refer to an interaction between an electron pair donor and a coordination site on a metal ion leading to an attractive force between the electron pair donor and the metal ion. The use of these terms is not intended to be limiting, in so much as certain coordinate bonds may also be classified as having more or less covalent character (if not entirely covalent character) depending on the nature of the metal ion and the electron pair donor.

The term "coordination site" is art-recognized and refers to a point on a metal ion that can accept an electron pair donated, for example, by a liquid or chelating agent.

The term "free coordination site" is art-recognized and refers to a coordination site on a metal ion that is vacant or occupied by a species that is weakly donating. Such species is readily displaced by another species, such as a Lewis base.

The term "coordination number" is art-recognized and refers to the number of coordination sites on a metal ion that are available for accepting an electron pair.

The term "coordination geometry" is art-recognized and refers to the manner in which coordination sites and free coordination sites are spatially arranged around a metal ion. Some examples of coordination geometry include octahedral, square planar, trigonal, trigonal biplanar and others known to those of skill in the art.

The term "complex" is art-recognized and means a compound formed by the union of one or more electron-rich and electron-poor molecules or atoms capable of independent existence with one or more electronically poor molecules or atoms, each of which is also capable of independent existence. A "coordination complex" is one type of a complex, in which there is a coordinate bond between a metal ion and an electron pair donor. A metal ion complex is a coordination complex in which the metal ion is a metal ion. In general, the terms "compound," "composition," "agent" and the like discussed herein include complexes, coordination complexes and metal ion complexes. As a general matter, the teachings of *Advanced Inorganic Chemistry* by Cotton and Wilkinson are referenced as supplementing the definitions herein in regard to coordination complexes and related matters.

In certain circumstances, a coordination complex may be understood to be composed of its constitutive components. For example, a coordination complex may have the following components: (i) one or more metal ions, which may or may not be the same atom, have the same charge, coordination number or coordination geometry and the like; and (ii) one or more Lewis bases that form coordinate bonds with the metal ion(s). Examples of such Lewis bases include chelating agents and ligands.

If a coordination complex is charged, in that the metal ion and any Lewis bases in the aggregate are not neutral, then such a complex will usually have one or more counterions to form a neutral compound. Such counterions may or may not be considered part of the coordination complex depending on how the term coordination complex is used. Counterions generally do not form coordinate bonds to the metal ion, although they may be associated, often in the solid state, with the metal ion or Lewis bases that make up the coordination complex. Some examples of counterions include monoanions such as nitrate, chloride, tetrafluororborate, hexafluorophosphate, and monocarboxylates, and dianions such as sulfate. In some cases, coordination complexes themselves may serve as counterions to another coordination complex.

The same chemical moiety may be either a ligand or a counterion to a coordination complex. For example, the anionic ligand chloride may be either coordinately bound to a metal ion or may act as a counterion without any need for bond formation. The exact form observed for chloride in any coordination complex will depend on a variety of factors including theoretical considerations such as kinetic versus thermodynamic effects, as well as the actual synthetic procedures utilized to make the coordination complex, such as the extent of reaction, acidity, concentration of chloride. These considerations are applicable to other counterions as well.

Additionally, a coordination complex may be solvated. Solvation refers to molecules, usually of solvent and often water, that associate with the coordination complex in the solid state. Again, as for counterions, such solvation molecules may or may not be considered part of the coordination complex depending on how the term coordination complex is used.

The term "synthetic" is art-recognized and refers to production by in vitro chemical or enzymatic synthesis.

The term "meso compound" is art-recognized and means a chemical compound which has at least two chiral centers but is achiral due to a plane or point of symmetry.

The term "chiral" is art-recognized and refers to molecules which have the property of non-superimposability of the mirror image partner, while the term "achiral" refers to molecules which are superimposable on their mirror image partner. A "prochiral molecule" is a molecule which has the potential to be converted to a chiral molecule in a particular process.

The term "stereoisomers" is art-recognized and refers to compounds which have identical chemical constitution, but differ with regard to the arrangement of the atoms or groups in space. In particular, "enantiomers" refer to two stereoisomers of a compound which are non-superimposable mirror images of one another. "Diastereomers", on the other hand, refers to stereoisomers with two or more centers of dissymmetry and whose molecules are not mirror images of one another.

Furthermore, a "stereoselective process" is one which produces a particular stereoisomer of a reaction product in preference to other possible stereoisomers of that product. An "enantioselective process" is one which favors production of one of the two possible enantiomers of a reaction product.

The term "regioisomers" is art-recognized and refers to compounds which have the same molecular Formula but differ in the connectivity of the atoms. Accordingly, a "regioselective process" is one which favors the production of a particular regioisomer over others, e.g., the reaction produces a statistically significant increase in the yield of a certain regioisomer.

The term "epimers" is art-recognized and refers to molecules with identical chemical constitution and containing more than one stereocenter, but which differ in configuration at only one of these stereocenters.

"Small molecule" is an art-recognized term. In certain embodiments, this term refers to a molecule which has a molecular weight of less than about 2000 amu, or less than about 1000 amu, and even less than about 500 amu.

The term "aliphatic" is an art-recognized term and includes linear, branched, and cyclic alkanes, alkenes, or alkynes. In certain embodiments, aliphatic groups in the present invention are linear or branched and have from 1 to about 20 carbon atoms.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

The term "heteroatom" is art-recognized and refers to an atom of any element other than carbon or hydrogen. Illustrative heteroatoms include boron, nitrogen, oxygen, phosphorus, sulfur and selenium.

The term "aryl" is art-recognized and refers to 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl", "heteroaryl", or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle" is art-recognized and refers to an aromatic or non-aromatic ring in which each atom of the ring is carbon.

The term "nitro" is art-recognized and refers to —NO$_2$; the term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to —SO$_2^-$. "Halide" designates the corresponding anion of the halogens, and "pseudohalide" has the definition set forth on 560 of "*Advanced Inorganic Chemistry*" by Cotton and Wilkinson.

The terms "amine" and "amino" are art-recognized and refer to both unsubstituted and substituted amines, e.g., a moiety that may be represented by the general formulas:

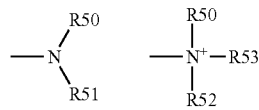

wherein R50, R51 and R52 each independently represent a hydrogen, an alkyl, an alkenyl, —(CH$_2$)$_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In certain embodiments, only one of R50 or R51 may be a carbonyl, e.g., R50, R51 and the nitrogen together do not form an imide. In other embodiments, R50 and R51 (and optionally R52) each independently represent a hydrogen, an alkyl, an alkenyl, or —(CH$_2$)$_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and refers to a moiety that may be represented by the general formula:

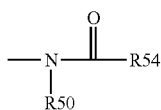

wherein R50 is as defined above, and R54 represents a hydrogen, an alkyl, an alkenyl or —(CH$_2$)$_m$—R61, where m and R61 are as defined above.

The term "amido" is art recognized as an amino-substituted carbonyl and includes a moiety that may be represented by the general formula:

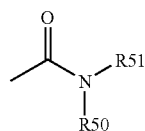

wherein R50 and R51 are as defined above. Certain embodiments of the amide in the present invention will not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—(CH$_2$)$_m$—R61, wherein m and R61 are defined above. Representative alkylthio groups include methylthio, ethyl thio, and the like.

The term "carbonyl" is art-recognized and includes such moieties as may be represented by the general formulas:

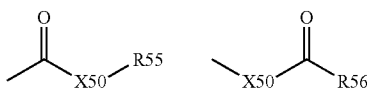

wherein X50 is a bond or represents an oxygen or a sulfur, and R55 represents a hydrogen, an alkyl, an alkenyl, —(CH$_2$)$_m$—R61, or a pharmaceutically acceptable salt. R56 represents a hydrogen, an alkyl, an alkenyl or —(CH$_2$)$_m$—R61, where m and R61 are defined above. Where X50 is an oxygen and R55 or R56 is not hydrogen, the Formula represents an "ester". Where X50 is an oxygen, and R55 is as defined above, the moiety is referred to herein as a carboxyl group, and particularly when R55 is a hydrogen, the Formula represents a "carboxylic acid". Where X50 is an oxygen, and R56 is hydrogen, the Formula represents a "formate". In general, where the oxygen atom of the above Formula is replaced by sulfur, the Formula represents a "thiocarbonyl" group. Where X50 is a sulfur and R55 or R56 is not hydrogen, the Formula represents a "thioester." Where X50 is a sulfur and R55 is hydrogen, the Formula represents a "thiocarboxylic acid." Where X50 is a sulfur and R56 is hydrogen, the Formula represents a "thioformate." On the other hand, where X50 is a bond, and R55 is not hydrogen, the above Formula represents a "ketone" group. Where X50 is a bond, and R55 is hydrogen, the above Formula represents an "aldehyde" group.

The term "carboxyl" is art recognized and includes such moieties as may be represented by the general formulas:

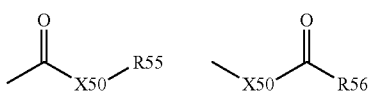

wherein X50 is a bond or represents an oxygen or a sulfur, and R55 and R56 represents a hydrogen, an alkyl, an alkenyl, —(CH$_2$)$_m$—R61 or a pharmaceutically acceptable salt, R56 represents a hydrogen, an alkyl, an alkenyl or —(CH$_2$)$_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—R61, where m and R61 are described above.

The term "sulfonate" is art recognized and refers to a moiety that may be represented by the general formula:

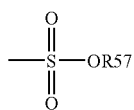

in which R57 is an electron pair, hydrogen, alkyl, cycloalkyl, or aryl.

The term "sulfate" is art recognized and includes a moiety that may be represented by the general formula:

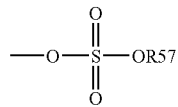

in which R57 is as defined above.

The term "sulfonamido" is art recognized and includes a moiety that may be represented by the general formula:

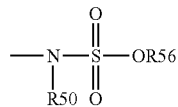

in which R50 and R56 are as defined above.

The term "sulfamoyl" is art-recognized and refers to a moiety that may be represented by the general formula:

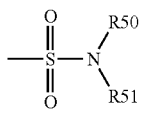

in which R50 and R51 are as defined above.

The term "sulfonyl" is art-recognized and refers to a moiety that may be represented by the general formula:

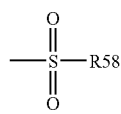

in which R58 is one of the following: hydrogen, alkyl, alkenyl, alkynyl, cycloalkyl, heterocyclyl, aryl or heteroaryl.

The term "sulfoxido" is art-recognized and refers to a moiety that may be represented by the general formula:

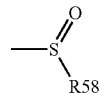

in which R58 is defined above.

The term "phosphoryl" is art-recognized and may in general be represented by the formula:

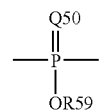

wherein Q50 represents S or O, and R59 represents hydrogen, a lower alkyl or an aryl. When used to substitute, e.g., an alkyl, the phosphoryl group of the phosphorylalkyl may be represented by the general formulas:

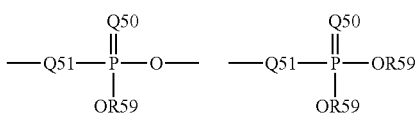

wherein Q50 and R59, each independently, are defined above, and Q51 represents O, S or N. When Q50 is S, the phosphoryl moiety is a "phosphorothioate".

The term "phosphoramidite" is art-recognized and may be represented in the general formulas:

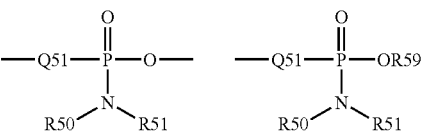

wherein Q51, R50, R51 and R59 are as defined above.

The term "phosphonamidite" is art-recognized and may be represented in the general formulas:

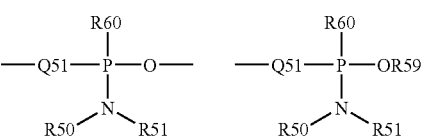

wherein Q51, R50, R51 and R59 are as defined above, and R60 represents a lower alkyl or an aryl. Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls. Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The definition of each expression, e.g. alkyl, m, n, and the like, when it occurs more than once in any structure, is intended to be independent of its definition elsewhere in the same structure.

The term "selenoalkyl" is art-recognized and refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—R61, m and R61 being defined above.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, *Handbook of Chemistry and Physics*, 67th Ed., 1986-87, inside cover.

The term "hydrocarbon" is art-recognized and includes all permissible compounds having at least one hydrogen and one carbon atom. For example, permissible hydrocarbons include acyclic and cyclic, branched and unbranched, carbocyclic and heterocyclic, aromatic and nonaromatic organic compounds that may be substituted or unsubstituted.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991). Protected forms of the inventive compounds are included within the scope of this invention.

The phrase "hydroxyl-protecting group" is art-recognized and includes those groups intended to protect a hydroxyl group against undesirable reactions during synthetic procedures and includes, for example, benzyl or other suitable esters or ethers groups known in the art.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma (a) constant. This well known constant is described in many references, for instance, March, *Advanced Organic Chemistry* 251-59, McGraw Hill Book Company, New York, (1977). The Hammett constant values are generally negative for electron donating groups ($\sigma(P)=-0.66$ for $NH_2$) and positive for electron withdrawing groups ($\sigma(P)=0.78$ for a nitro group), $\sigma(P)$ indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

By the terms "amino acid residue" and "peptide residue" is meant an amino acid or peptide molecule without the —OH of its carboxyl group. In general the abbreviations used herein for designating the amino acids and the protective groups are based on recommendations of the IUPAC-IUB Commission on Biochemical Nomenclature (see Biochemistry (1972) 11:1726-1732). For instance Met, Ile, Leu, Ala and Gly represent "residues" of methionine, isoleucine, leucine, alanine and glycine, respectively. By the residue is meant a radical derived from the corresponding α-amino acid by eliminating the OH portion of the carboxyl group and the H portion of the α-amino group. The term "amino acid side chain" is that part of an amino acid exclusive of the —$CH(NH_2)COOH$ portion, as defined by Kopple, *Peptides and Amino Acids* 2, 33 (W. A. Benjamin Inc., New York and Amsterdam, 1966); examples of such side chains of the common amino acids are —$CH_2CH_2SCH_3$ (the side chain of methionine), —$CH_2CH(CH_3)_2$ (the side chain of leucine) or —H (the side chain of glycine).

The term "amino acid" is intended to embrace all compounds, whether natural or synthetic, which include both an amino functionality and an acid functionality, including amino acid analogs and derivatives. In certain embodiments, the amino acids used in the application of this invention are those naturally occurring amino acids found in proteins, or the naturally occurring anabolic or catabolic products of such amino acids which contain amino and carboxyl groups. Particularly suitable amino acid side chains include side chains selected from those of the following amino acids: glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan.

The term "amino acid residue" further includes analogs, derivatives and congeners of any specific amino acid referred to herein, as well as C-terminal or N-terminal protected amino acid derivatives (e.g. modified with an N-terminal or C-terminal protecting group). For example, the present invention contemplates the use of amino acid analogs wherein a side chain is lengthened or shortened while still providing a carboxyl, amino or other reactive precursor functional group for cyclization, as well as amino acid analogs having variant side chains with appropriate functional groups. For instance, the subject compounds may include an amino acid analog such as, for example, cyanoalanine, canavanine, djenkolic acid, norleucine, 3-phosphoserine, homoserine, dihydroxyphenylalanine, 5-hydroxytryptophan, 1-methylhistidine, 3-methylhistidine, diaminopimelic acid, ornithine, or diaminobutyric acid. Other naturally occurring amino acid metabolites or precursors having side chains which are suitable herein will be recognized by those skilled in the art and are included in the scope of the present invention.

Also included are the (D) and (L) stereoisomers of such amino acids when the structure of the amino acid admits of stereoisomeric forms. The configuration of the amino acids and amino acid residues herein are designated by the appropriate symbols (D), (L) or (DL), furthermore when the configuration is not designated the amino acid or residue can have the configuration (D), (L) or (DL). It will be noted that the structure of some of the compounds of this invention includes asymmetric carbon atoms. It is to be understood accordingly that the isomers arising from such asymmetry are included within the scope of this invention. Such isomers may be obtained in substantially pure form by classical separation techniques and by sterically controlled synthesis. For the purposes of this application, unless expressly noted to the contrary, a named amino acid shall be construed to include both the (D) or (L) stereoisomers. In the majority of cases, D- and L-amino acids have R- and S-absolute configurations, respectively.

The names of the natural amino acids are abbreviated herein in accordance with the recommendations of IUPAC-IUB.

The term "antibody" is art-recognized and intended to include whole antibodies, e.g., of any isotype (IgG, IgA, IgM, IgE, etc.), and includes fragments thereof which are also specifically reactive with a vertebrate, e.g., mammalian, protein. Antibodies may be fragmented using conventional techniques and the fragments screened for utility in the same manner as described above for whole antibodies. Thus, the term includes segments of proteolytically-cleaved or recombinantly-prepared portions of an antibody molecule that are capable of selectively reacting with a certain protein. Non-limiting examples of such proteolytic and/or recombinant fragments include Fab, F(ab')2, Fab', Fv, and single chain antibodies (scFv) containing a V[L] and/or V[H] domain joined by a peptide linker. The scFv's may be covalently or non-covalently linked to form antibodies having two or more binding sites. The subject invention includes polyclonal, monoclonal or other purified preparations of antibodies and recombinant antibodies.

The terms "human monoclonal antibodies" and "humanized" murine antibodies, are art-recognized and refer to murine monoclonal antibodies "humanized" by genetically recombining the nucleotide sequence encoding the murine Fv region (i.e., containing the antigen binding site) or the complementarity-determining regions thereof with the nucleotide sequence encoding at least a human constant domain region and an Fc region, e.g., in a manner similar to that disclosed in European Patent Application Publication No. 0,411,893 A3. Some additional murine residues may also be retained within the human variable region framework domains to ensure proper target site binding characteristics. In certain embodiments, humanized antibodies may decrease the immunoreactivity of the antibody or polypeptide in the host recipient, permitting an increase in the half-life and a reduction in the possibility of adverse immune reactions.

The term "target" is art-recognized and means a site to which targeted constructs bind. A target may be either in vivo or in vitro. In certain embodiments, a target may be a tumor (e.g., tumors of the brain, lung (small cell and non-small cell), ovary, prostate, breast and colon as well as other carcinomas and sarcomas). In other embodiments, a target may be a site of infection (e.g., by bacteria, viruses (e.g., HIV, herpes, hepatitis) and pathogenic fingi (*Candida* sp.). Certain target infectious organisms include those that are drug resistant (e.g., Enterobacteriaceae, *Enterococcus, Haemophilus influenza, Mycobacterium tuberculosis, Neisseria gonorrhoeae, Plasmodium falciparum, Pseudomonas aeruginosa, Shigella dysenteriae, Staphylococcus aureus, Streptococcus pneumoniae*). In still other embodiments, a target may refer to a molecular structure to which a targeting moiety binds, such as a hapten, epitope, receptor, dsDNA fragment, carbohydrate or enzyme. Additionally, a target may be a type of tissue, e.g., neuronal tissue, intestinal tissue, pancreatic tissue etc.

The term "target cell", which is art-recognized, and which cells may serve as the target for methods of the present invention, include prokaryotes and eukaryotes, including yeasts, plant cells and animal cells. Target cells may include, for example, the cells lining the alimentary canal, such as the oral and pharyngeal mucosa, cells forming the villi of the small intestine, cells lining the large intestine, cells lining the respiratory system (nasal passages/lungs) of an animal (which may be contacted by inhalation of the subject invention), dermal/epidermal cells, cells of the vagina and rectum, cells of internal organs including cells of the placenta and the so-called blood/brain barrier, etc.

The term "targeting moiety" is art-recognized and refers to any molecular structure which assists the construct in localizing to a particular target area, entering a target cell(s), and/or binding to a target receptor. For example, lipids (including cationic, neutral, and steroidal lipids, virosomes, and liposomes), antibodies, lectins, ligands, sugars, steroids, hormones, nutrients, and proteins may serve as targeting moieties.

A "patient," "subject", or "host" to be treated by the subject method is art-recognized, and means either a human or non-human animal.

The term "bioavailable" is art-recognized and means that a compound the subject invention is in a form that allows for it, or a portion of the amount administered, to be absorbed by, incorporated to, or otherwise physiologically available to a subject or patient to whom it is administered.

The term "treating" is an art-recognized term which includes curing as well as ameliorating at least one symptom of any condition or disease. Diagnostic applications are also examples of "treating".

The phrase "pharmaceutically acceptable" is art-recognized. In certain embodiments, the term includes compositions, fluorescein-based ligands and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any supplement or composition, or component thereof, from one organ, or portion of the body, to another organ, or portion of the body. Each carrier must be "acceptable" in the sense of being compatible with the other ingredients of the supplement and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical Formulations.

The term "pharmaceutically acceptable salts" is art-recognized, and includes relatively non-toxic, inorganic and organic acid addition salts of compositions of the present invention, including without limitation, therapeutic agents, excipients, other materials and the like. Examples of pharmaceutically acceptable salts include those derived from mineral acids, such as hydrochloric acid and sulfuric acid, and those derived from organic acids, such as ethanesulfonic acid, benzenesulfonic acid, p-toluenesulfonic acid, and the like. Examples of suitable inorganic bases for the formation of salts include the hydroxides, carbonates, and bicarbonates of ammonia, sodium, lithium, potassium, calcium, magnesium, aluminum, zinc and the like. Salts may also be formed with suitable organic bases, including those that are non-toxic and strong enough to form such salts. For purposes of illustration, the class of such organic bases may include mono-, di-, and trialkylamines, such as methylamine, dimethylamine, and triethylamine; mono-, di- or trihydroxyalkylamines such as mono-, di-, and triethanolamine; amino acids, such as arginine and lysine; guanidine; N-methylglucosamine; N-methylglucamine; L-glutamine; N-methylpiperazine; morpholine; ethylenediamine; N-benzylphenethylamine; (trihydroxymethyl)aminoethane; and the like. See, for example, *J. Pharm. Sci.*, 66:1-19 (1977).

The phrases "systemic administration," "administered systemically," "peripheral administration" and "administered peripherally" are art-recognized, and include the administration of a subject supplement, composition, therapeutic or other material other than directly into the central nervous system, e.g., by subcutaneous administration, such that it enters the patient's system and, thus, is subject to metabolism and other like processes.

The phrase "therapeutically effective amount" is an art-recognized term. In certain embodiments, the term refers to an amount of the therapeutic agent that produces some desired effect at a reasonable benefit/risk ratio applicable to any medical treatment. In certain embodiments, the term refers to that amount necessary or sufficient for diagnostic use of the subject compositions. One of ordinary skill in the art may empirically determine the effective amount of a particular compound without necessitating undue experimentation.

The term "$ED_{50}$" is art-recognized. In certain embodiments, $ED_{50}$ means the dose of a drug which produces 50% of its maximum response or effect, or alternatively, the dose which produces a pre-determined response in 50% of test subjects or preparations. The term "$LD_{50}$" is art-recognized. In certain embodiments, $LD_{50}$ means the dose of a drug which is lethal in 50% of test subjects. The term "therapeutic index" is an art-recognized term which refers to the therapeutic index of a drug, defined as $LD_{50}/ED_{50}$.

Contemplated equivalents of the fluorescein-based ligands, scaffold molecules and other compositions described herein include such materials which otherwise correspond thereto, and which have the same general properties thereof, wherein one or more simple variations of substituents are made which do not adversely affect the efficacy of such molecule to achieve its intended purpose. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

II. GENERAL DESCRIPTION OF FLUORESCEIN-BASED LIGANDS

A variety of fluorescein-based ligands, and methods of using and making the same, are contemplated by the present invention. In certain embodiments, the subject ligands form coordination complexes with a variety of metal ions, in particular copper (II), with a concomitant change in the fluorescent properties of the resulting metal complex as compared to the uncomplexed ligand. In certain embodiment, such ligands may be used to assay for metal ions including as non-limiting examples heavy metal ions. A variety of methods of preparing such ligands and the coordination complexes, of assaying for the binding activity of such ligands, and of using such compositions are also taught by the subject invention. A number of different ligands and metal ions are contemplated for the subject coordination complexes, as set out in more detail below.

The carbon positions at which substitutions are able to be made on a fluorescein molecule are numbered according to the system shown in the figure below. This system is known to those of skill in the art, and will be used to refer to various atoms of the fluorescein molecules in the description, exemplification, and claims below.

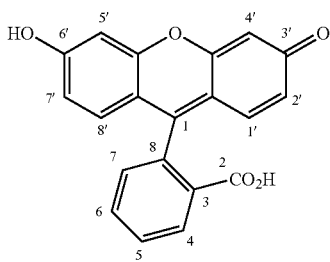

By way of a general, non-limiting description, fluorescein exists in three isomeric forms that are favored under different conditions shown below. The free acid is favorable under aqueous conditions and in polar solvents, the lactone is present in non-polar media, and the zwitterion is an isolable intermediate. Addition of acetate, benzoate or silyl protecting groups to the phenols imposes the lactone isomer. In a stable lactone form, fluoresceins may be purified by standard experimental techniques and identified by NMR and IR spectroscopy. In general, it is the deprotonated free acid form of fluorescein that accounts for the compounds' strong fluorescence.

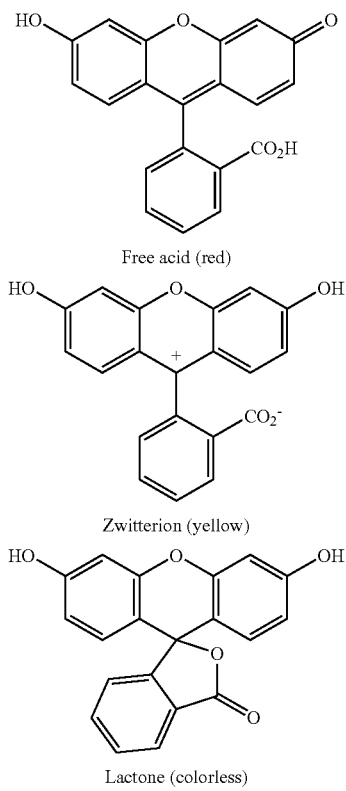

Free acid (red)

Zwitterion (yellow)

Lactone (colorless)

III. FLUORESCEIN-BASED SENSORS (A) Uncomplexed Sensors

One aspect of the invention relates to a compound represented by formula I:

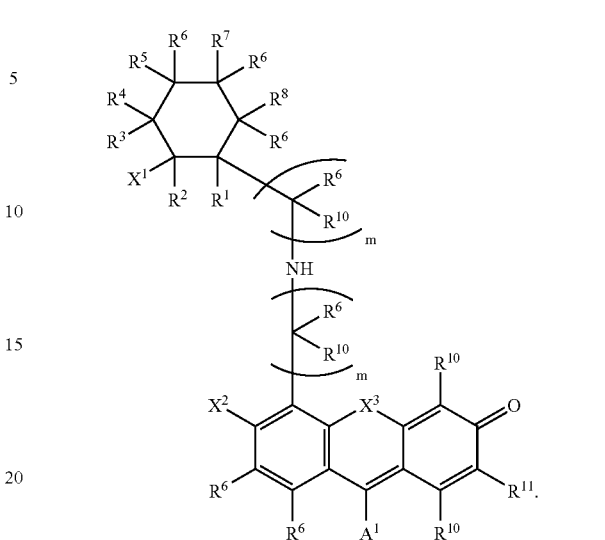

$A^1$ is aryl or heteroaryl, both of which are optionally substituted with one or more of halogen, alkoxyl, —OH, —N($R^{12}$)$_2$, —COR$^{12}$, —CO$_2$R$^{12}$, —N($R^{12}$)C(O)R$^{12}$, or —C(O)N($R^{12}$)$_2$;

$X^1$ is —OR$^9$, —SR$^9$, —N=R$^9$, or —N(R$^{13}$)R$^9$;

$X^2$ is —OR$^3$, —SR$^{13}$, or —N(R$^{13}$)$_2$;

$X^3$ is —O—, —S—, or —N(R$^{13}$)—;

$R^1$, $R^3$, $R^5$, $R^7$, $R^8$ and $R^{10}$ each represent independently for each occurrence H, alkyl, aryl or heteroaryl; or $R^1$ and $R^8$ taken together form a bond; or $R^5$ and $R^7$ taken together form a bond;

$R^2$, $R^4$, and $R^6$ each represent independently for each occurrence H, alkyl, aryl, heteroaryl, aralkyl, halogen, alkoxyl, —COR$^{12}$, or —CO$_2$R$^{12}$; or $R^2$ and $R^3$ taken together form a bond; or $R^4$ and $R^9$ taken together form a 5-6 member ring optionally substituted with one or more of alkyl, hydroxyalkyl, aryl, aralkyl, halogen, alkoxyl, —N($R^9$)$_2$, —COR$^9$, —CO$_2$R$^9$, —N($R^9$)C(O)R$^9$, or —C(O)N($R^9$)$_2$;

$R^9$ is H, alkyl, aryl, heteroaryl, or aralkyl;

$R^{11}$ is H, alkyl, aryl, heteroaryl, aralkyl, or halogen;

$R^{12}$ represents independently for each occurrence H, alkyl, aryl, heteroaryl, or aralkyl;

$R^{13}$ represents independently for each occurrence H or ($C_1$-$C_6$)alkyl;

m represents independently for each occurrence 0, 1, 2, 3, or 4; and the stereochemical configuration at any stereocenter of a compound represented by I is R, S, or a mixture of these configurations.

In certain embodiments, the present invention relates to compound I, wherein $A^1$ is aryl optionally substituted with —CO$_2$R$^{12}$.

In certain embodiments, the present invention relates to compound I, wherein $X^1$ is —N=R$^9$.

In certain embodiments, the present invention relates to compound I, wherein $X^2$ is —OR$^{13}$.

In certain embodiments, the present invention relates to compound I, wherein $X^3$ is —O—.

In certain embodiments, the present invention relates to compound I, wherein $R^1$ and $R^8$ taken together form a bond.

In certain embodiments, the present invention relates to compound I, wherein $R^5$ and $R^7$ taken together form a bond.

In certain embodiments, the present invention relates to compound I, wherein $R^{10}$ is H or alkyl.

In certain embodiments, the present invention relates to compound I, wherein $R^2$ and $R^3$ taken together form a bond.

In certain embodiments, the present invention relates to compound I, wherein $R^4$ and $R^9$ taken together form a 5-6 member ring optionally substituted with one or more of alkyl, aryl, aralkyl, or halogen.

In certain embodiments, the present invention relates to compound I, wherein $R^6$ is H or alkyl.

In certain embodiments, the present invention relates to compound I, wherein $R^{11}$ is halogen.

In certain embodiments, the present invention relates to compound I, wherein $R^{12}$ is H.

In certain embodiments, the present invention relates to compound I, wherein $R^{13}$ is H.

In certain embodiments, the present invention relates to compound I, wherein m is 0 or 1.

In certain embodiments, the present invention relates to compound I, wherein $A^1$ is aryl optionally substituted with —$CO_2R^{12}$, $X^1$ is —N=$R^9$, $X^2$ is —$OR^{13}$, $X^3$ is —O—, and $R^4$ and $R^9$ taken together form a 5-6 member ring optionally substituted with one or more of alkyl, aryl, aralkyl, or halogen.

In certain embodiments, the present invention relates to compound I, wherein $A^1$ is aryl optionally substituted with —$CO_2R^{12}$; $X^1$ is —N=$R^9$, $X^2$ is —$OR^{13}$; $X^3$ is —O—; $R^4$ and $R^9$ taken together form a 5-6 member ring optionally substituted with one or more of alkyl, aryl, aralkyl, or halogen; $R^6$ and $R^{10}$ each represent independently for each occurrence H or alkyl; $R^{11}$ is halogen; and $R^{10}$ and $R^{12}$ are H.

In certain embodiments, the present invention relates to compound I, wherein said compound of formula I is represented by formula Ia:

Ia wherein, $A^1$ is aryl or heteroaryl, both of which are optionally substituted with one or more of halogen, alkoxyl, —OH, —$N(R^8)_2$, —$COR^8$, or —$CO_2R^8$;

$X^1$ is —$OR^6$, —$SR^6$, or —$N(R^6)_2$;

$X^2$ is —O—, —S—, or —$N(R^6)$—;

$R^1$ represents independently for each occurrence H, alkyl, hydroxyalkyl, aryl, aralkyl, halogen, alkoxyl, —$N(R^8)_2$, —$COR^8$, —$CO_2R^8$, —$N(R^9)C(O)R^8$, or —$C(O)N(R^8)_2$;

$R^2$, $R^3$, and $R^5$ each represent independently for each occurrence H, alkyl, halogen, alkoxyl, —$COR^8$, or —$CO_2R^8$;

$R^4$ and $R^6$ each represent independently for each occurrence H or alkyl;

$R^7$ is halogen;

$R^8$ represents independently for each occurrence H, alkyl, aryl, heteroaryl, or aralkyl;

m represents independently for each occurrence 0, 1, or 2; and the stereochemical configuration at any stereocenter of a compound represented by Ia is R, S, or a mixture of these configurations.

In certain embodiments, the present invention relates to compound Ia, wherein $A^1$ is aryl optionally substituted with one or more of —$COR^8$.

In certain embodiments, the present invention relates to compound Ia, wherein $X^1$ is —$OR^6$.

In certain embodiments, the present invention relates to compound Ia, wherein $X^2$ is —O—.

In certain embodiments, the present invention relates to compound Ia, wherein $R^1$, $R^2$, $R^3$, and $R^5$ each represent independently for each occurrence H or alkyl.

In certain embodiments, the present invention relates to compound Ia, wherein $R^4$ and $R^6$ are H.

In certain embodiments, the present invention relates to compound Ia, wherein $R^7$ is chloride.

In certain embodiments, the present invention relates to compound Ia, wherein $R^8$ represents independently for each occurrence H or alkyl.

In certain embodiments, the present invention relates to compound Ia, wherein $A^1$ is aryl optionally substituted with —$COR^8$, $X^1$ is —$OR^6$, and $X^2$ is —O—.

In certain embodiments, the present invention relates to compound Ia, wherein $A^1$ is aryl optionally substituted with —$COR^8$; $X^1$ is —$OR^6$; $X^2$ is —O—; $R^1$, $R^2$, $R^3$, and $R^5$ each represent independently for each occurrence H or alkyl; $R^4$ and $R^6$ are H; and $R^7$ is chloride.

In certain embodiments, the present invention relates to compound Ia, wherein $A^1$ is aryl optionally substituted with —$COR^8$; $X^1$ is —$OR^6$; $X^2$ is —O—; $R^1$, $R^2$, $R^3$, and $R^5$ each represent independently for each occurrence H or alkyl; $R^4$ and $R^6$ are H; $R^7$ is chloride; $R^8$ is H; and m represents independently for each occurrence 0 or 1.

In certain embodiments, the present invention relates to compound I, wherein said compound of formula I is one of the following:

-continued
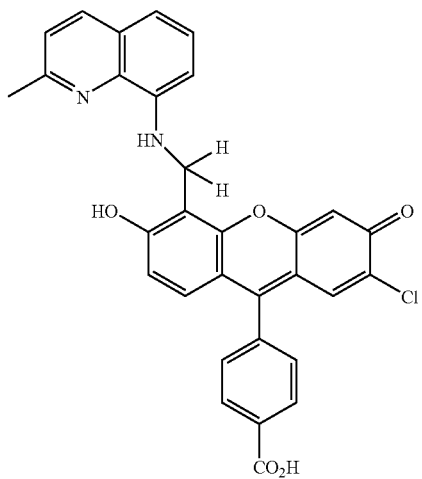
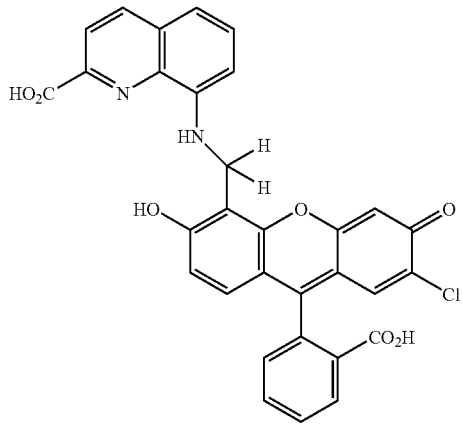
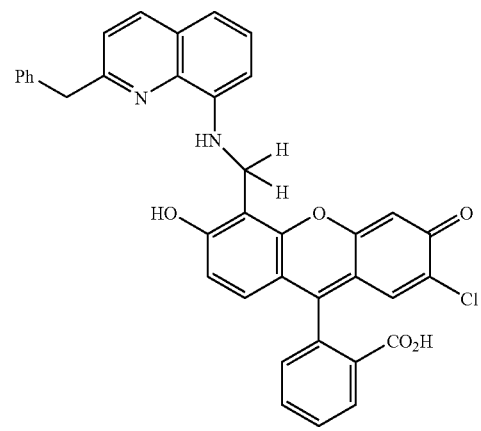
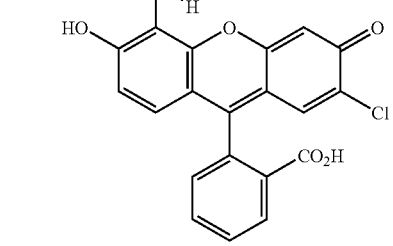
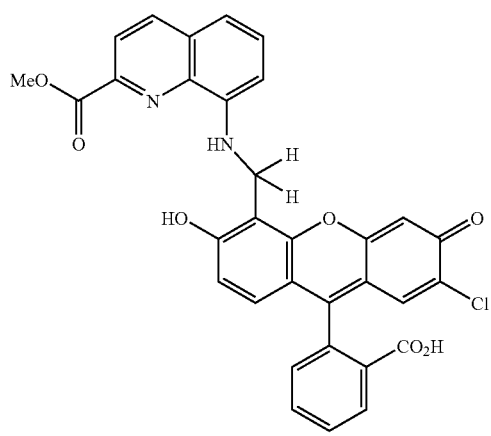
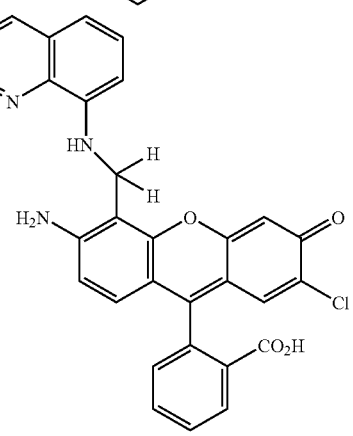

-continued

-continued
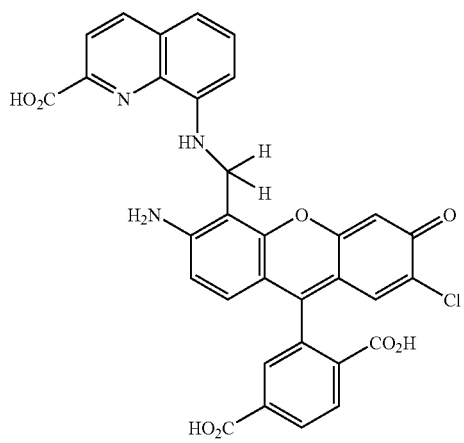
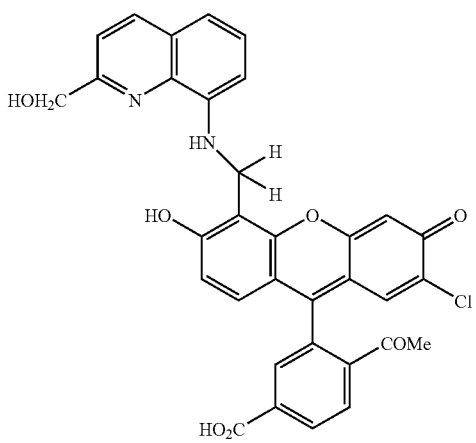

-continued
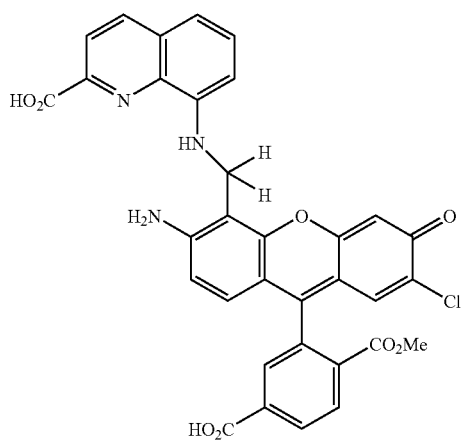
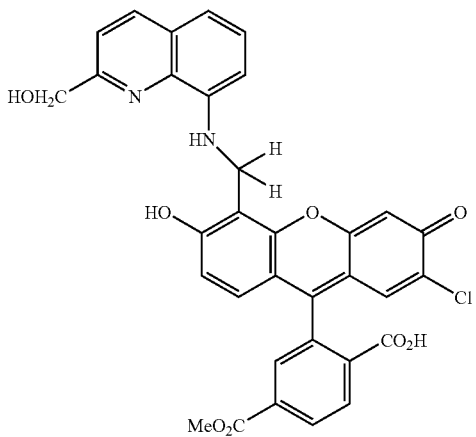

-continued
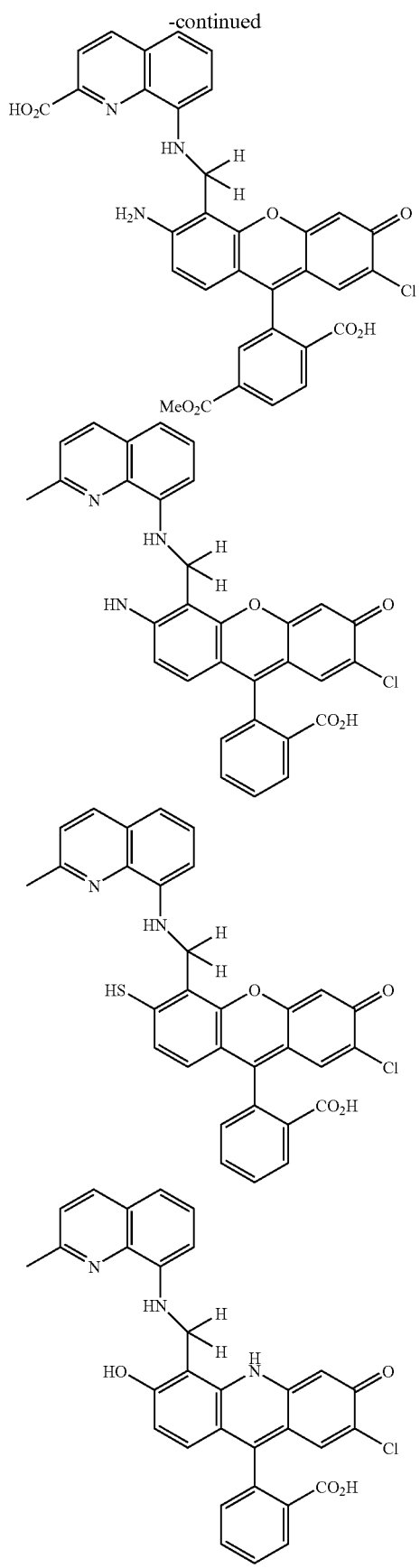
-continued
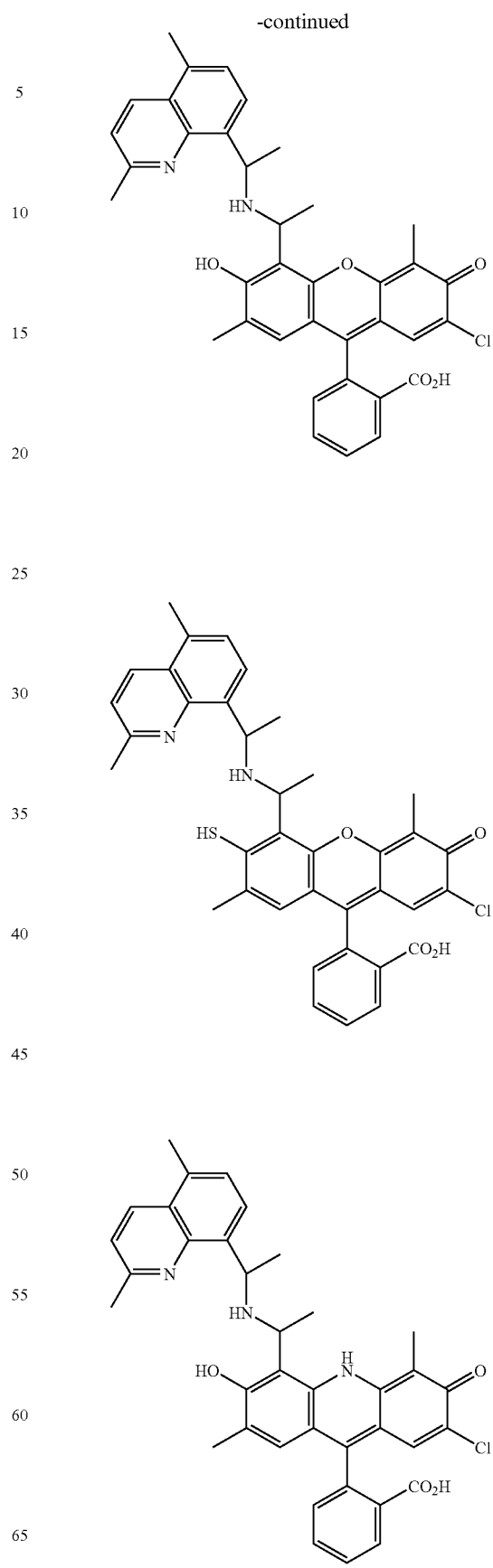

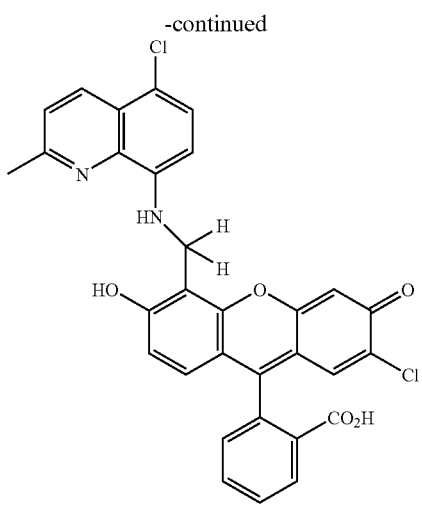
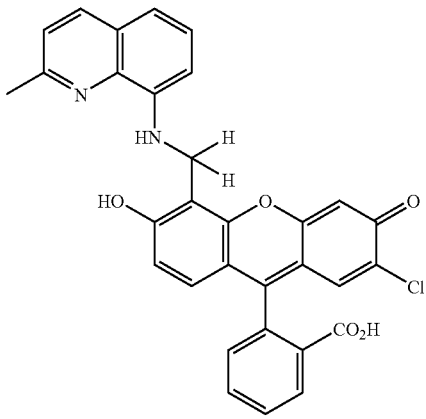
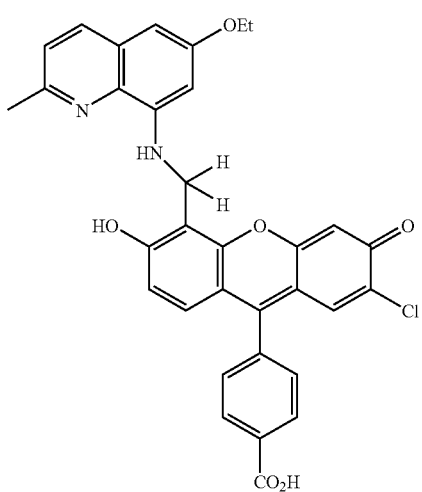
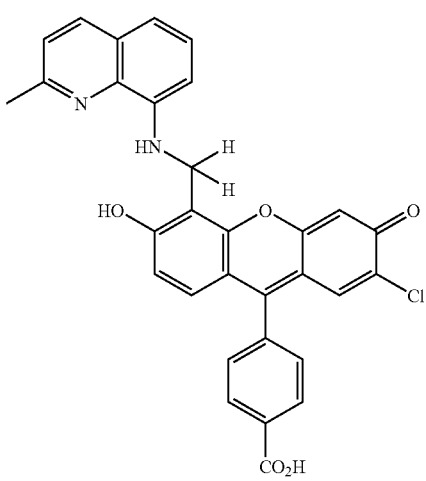
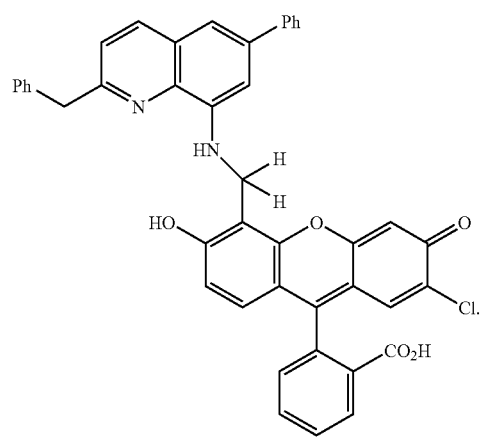
In certain embodiments, the present invention relates to compound I, wherein said compound of formula I is one of the following:

-continued
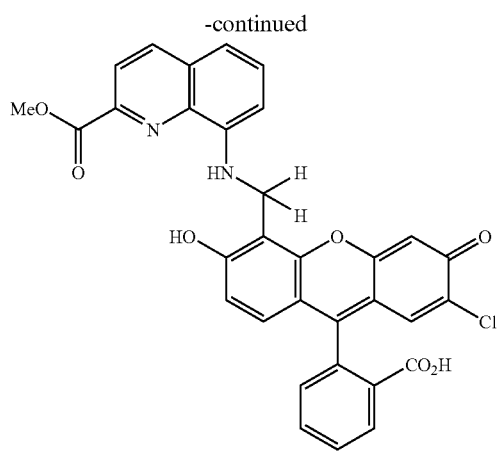
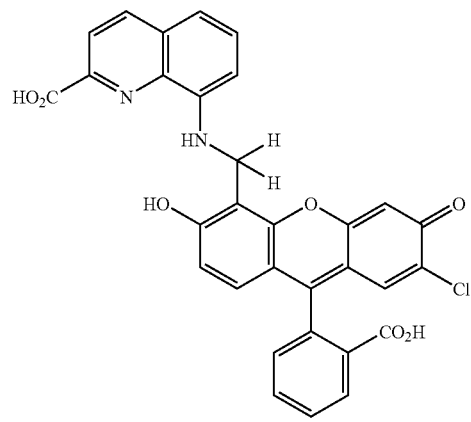
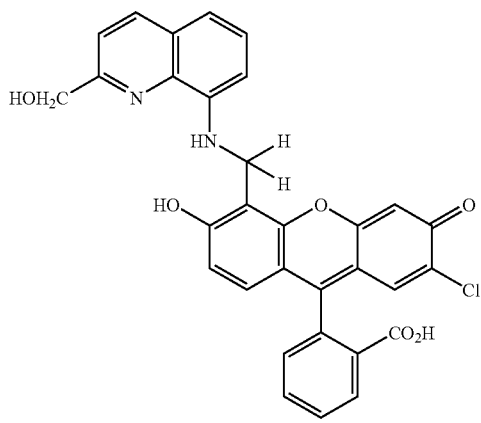
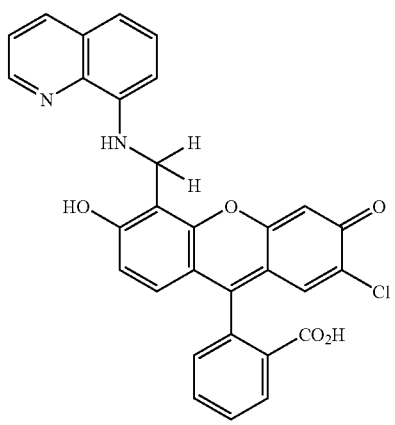
-continued
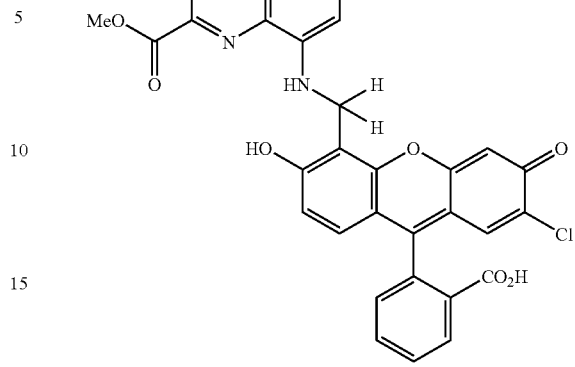
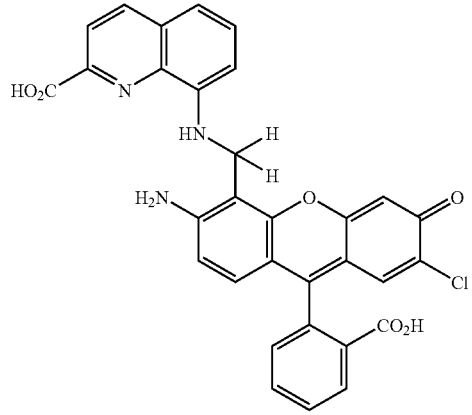
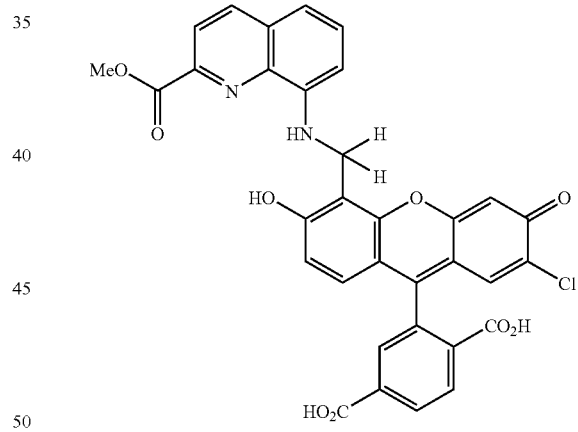
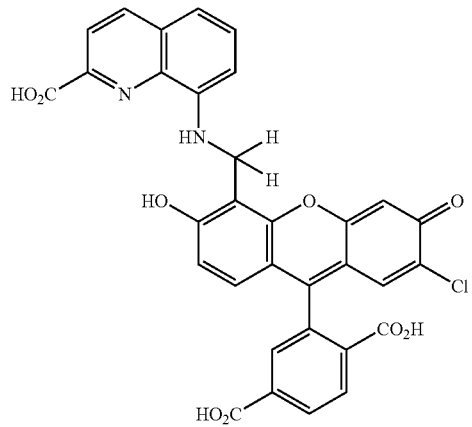

-continued
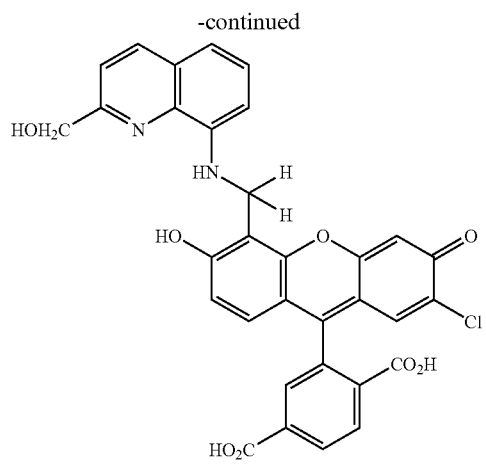
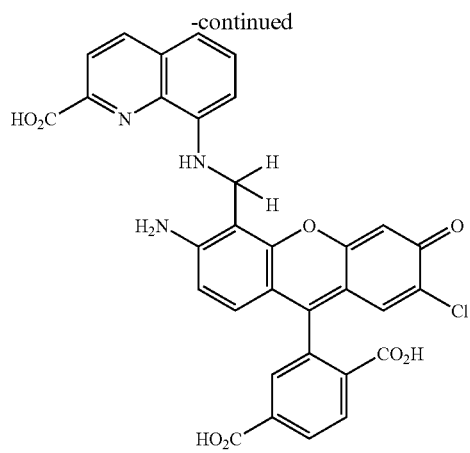
In certain embodiments, the present invention relates to compound I, wherein said compound of formula I is:
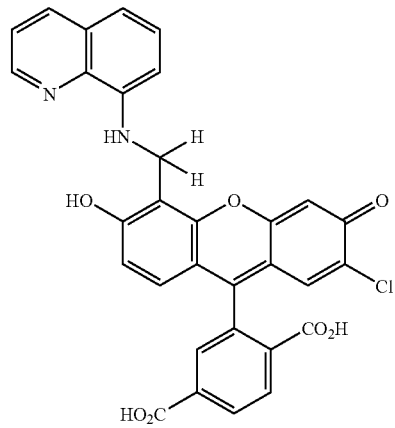
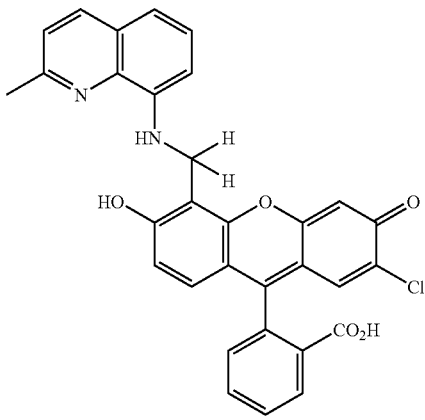
(B) Sensors Complexed with a Transition Metal
Another aspect of the invention relates to a compound represented by formula II:
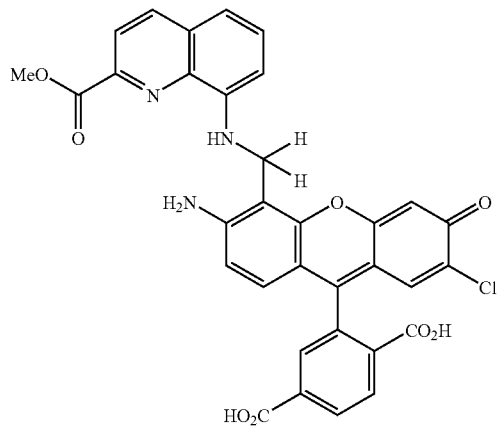
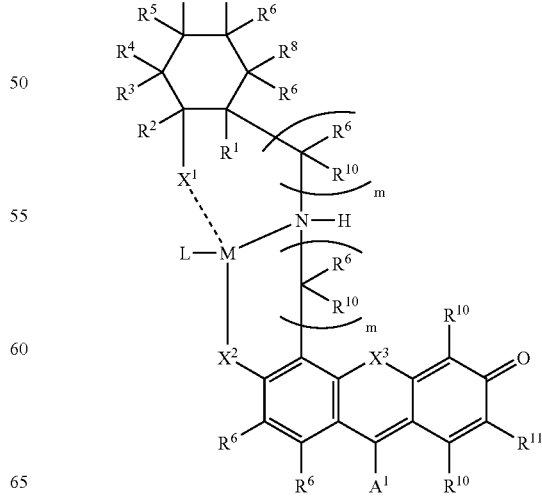

$A^1$ is aryl or heteroaryl, both of which are optionally substituted with one or more of halogen, alkoxyl, —OH, —N($R^{12}$)$_2$, —COR$^{12}$, —CO$_2$R$^{12}$, —N($R^{12}$)C(O)R$^{12}$, or —C(O)N($R^{12}$)$_2$;

L is a ligand;

M is a transition metal;

$X^1$ is —OR$^9$, —SR$^9$, —N═R$^9$, or —N($R^{13}$)R$^9$;

$X^2$ is —O—, —S—, or —N($R^{13}$)—;

$X^3$ is —O—, —S—, or —N($R^{13}$)—;

$R^1$, $R^3$, $R^5$, $R^7$, $R^8$ and $R^{10}$ each represent independently for each occurrence H, alkyl, aryl or heteroaryl; or $R^1$ and $R^8$ taken together form a bond; or $R^5$ and $R^7$ taken together form a bond;

$R^2$, $R^4$, and $R^6$ each represent independently for each occurrence H, alkyl, aryl, heteroaryl, aralkyl, halogen, alkoxyl, —COR$^{12}$, or —CO$_2$R$^{12}$; or $R^2$ and $R^3$ taken together form a bond; or $R^4$ and $R^9$ taken together form a 5-6 member ring optionally substituted with one or more of alkyl, hydroxyalkyl, aryl, aralkyl, halogen, alkoxyl, —N($R^9$)$_2$, —COR$^9$, —CO$_2$R$^9$, —N($R^9$)C(O)R$^9$, or —C(O)N($R^9$)$_2$;

$R^9$ is H, alkyl, aryl, heteroaryl, or aralkyl;

$R^{11}$ is H, alkyl, aryl, heteroaryl, aralkyl, or halogen;

$R^{12}$ represents independently for each occurrence H, alkyl, aryl, heteroaryl, or aralkyl;

$R^{13}$ represents independently for each occurrence H or ($C_1$-$C_6$)alkyl;

m represents independently for each occurrence 0, 1, 2, 3, or 4; and the stereochemical configuration at any stereocenter of a compound represented by II is R, S, or a mixture of these configurations.

In certain embodiments, the present invention relates to compound II, wherein $A^1$ is aryl optionally substituted with —CO$_2$R$^{12}$.

In certain embodiments, the present invention relates to compound II, wherein $X^1$ is —N═R$^9$.

In certain embodiments, the present invention relates to compound II, wherein $X^2$ is —O—.

In certain embodiments, the present invention relates to compound II, wherein $X^3$ is —O—.

In certain embodiments, the present invention relates to compound II, wherein $R^1$ and $R^8$ taken together form a bond.

In certain embodiments, the present invention relates to compound II, wherein $R^5$ and $R^7$ taken together form a bond.

In certain embodiments, the present invention relates to compound II, wherein $R^{10}$ is H or alkyl.

In certain embodiments, the present invention relates to compound II, wherein $R^2$ and $R^3$ taken together form a bond.

In certain embodiments, the present invention relates to compound II, wherein $R^4$ and $R^9$ taken together form a 5-6 member ring optionally substituted with one or more of alkyl, aryl, aralkyl, or halogen.

In certain embodiments, the present invention relates to compound II, wherein $R^6$ is H or alkyl.

In certain embodiments, the present invention relates to compound II, wherein $R^{11}$ is halogen.

In certain embodiments, the present invention relates to compound II, wherein $R^{12}$ is H.

In certain embodiments, the present invention relates to compound II, wherein $R^{13}$ is H.

In certain embodiments, the present invention relates to compound II, wherein m is 0 or 1.

In certain embodiments, the present invention relates to compound II, wherein $A^1$ is aryl optionally substituted with —CO$_2$R$^{12}$, $X^1$ is —N═R$^9$, $X^2$ is —OR$^{13}$, $X^3$ is —O—, and $R^4$ and $R^9$ taken together form a 5-6 member ring optionally substituted with one or more of alkyl, aryl, aralkyl, or halogen.

In certain embodiments, the present invention relates to compound II, wherein $A^1$ is aryl optionally substituted with —CO$_2$R$^{12}$; $X^1$ is —N═R$^9$, $X^2$ is —OR$^{13}$; $X^3$ is —O—; $R^4$ and $R^9$ taken together form a 5-6 member ring optionally substituted with one or more of alkyl, aryl, aralkyl, or halogen; $R^6$ and $R^{10}$ each represent independently for each occurrence H or alkyl; $R^{11}$ is halogen; and $R^{10}$ and $R^{12}$ are H.

In certain embodiments, the present invention relates to compound II, wherein M is Cu, Co, Fe, Ni, Zn, Ru, or Rh.

In certain embodiments, the present invention relates to compound II, wherein M is Cu, Co, Ru, or Rh.

In certain embodiments, the present invention relates to compound II, wherein M is Cu.

In certain embodiments, the present invention relates to compound II, wherein L is halogen, alkoxy, —OC(O)alkyl, —OC(O)aryl, or —OC(O)aralkyl.

In certain embodiments, the present invention relates to compound II, wherein L is halogen.

In certain embodiments, the present invention relates to compound II, wherein said compound of formula II is represented by formula Ia:

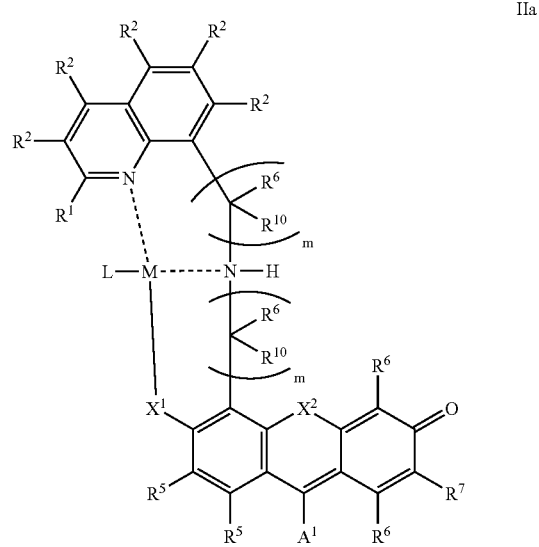

IIa wherein, $A^1$ is aryl or heteroaryl, both of which are optionally substituted with one or more of halogen, alkoxyl, —OH, —N($R^8$)$_2$, —COR$^8$, or —CO$_2$R$^8$;

L is a ligand;

M is a transition metal;

$X^1$ is —O—, —S—, or —N($R^6$)—;

$X^2$ is —O—, —S—, or —N($R^6$)—;

$R^1$ represents independently for each occurrence H, alkyl, hydroxyalkyl, aryl, aralkyl, halogen, alkoxyl, —N($R^8$)$_2$, —COR$^8$, —CO$_2$R$^8$, —N($R^8$)C(O)R$^8$, or —C(O)N($R^8$)$_2$;

$R^2$, $R^3$, and $R^5$ each represent independently for each occurrence H, alkyl, halogen, alkoxyl, —COR$^8$, or —CO$_2$R$^8$;

$R^4$ and $R^6$ each represent independently for each occurrence H or alkyl;

$R^7$ is halogen;

$R^8$ represents independently for each occurrence H, alkyl, aryl, heteroaryl, or aralkyl;

m represents independently for each occurrence 0, 1, or 2;

the stereochemical configuration at any stereocenter of a compound represented by IIa is R, S, or a mixture of these configurations; and $R^1$ is optionally coordinated to M.

In certain embodiments, the present invention relates to compound Ia, wherein $A^1$ is aryl optionally substituted with one or more of —$COR^8$.

In certain embodiments, the present invention relates to compound Ia, wherein $X^1$ is —O—.

In certain embodiments, the present invention relates to compound Ia, wherein $X^2$ is —O—.

In certain embodiments, the present invention relates to compound IIa, wherein $R^1$, $R^2$, $R^3$, and $R^5$ each represent independently for each occurrence H or alkyl.

In certain embodiments, the present invention relates to compound Ia, wherein $R^4$ and $R^6$ are H.

In certain embodiments, the present invention relates to compound Ia, wherein $R^7$ is chloride.

In certain embodiments, the present invention relates to compound IIa, wherein $R^8$ represents independently for each occurrence H or alkyl.

In certain embodiments, the present invention relates to compound Ia, wherein $A^1$ is aryl optionally substituted with —$COR^8$, $X^1$ is —$OR^6$, and $X^2$ is —O—.

In certain embodiments, the present invention relates to compound Ia, wherein $A^1$ is aryl optionally substituted with —$COR^8$; $X^1$ is —O—; $X^2$ is —O—; $R^1$, $R^2$, $R^3$, and $R^5$ each represent independently for each occurrence H or alkyl; $R^4$ and $R^6$ are H; and $R^7$ is chloride.

In certain embodiments, the present invention relates to compound Ia, wherein $A^1$ is aryl optionally substituted with —$COR^8$; $X^1$ is —O—; $X^2$ is —O—; $R^1$, $R^2$, $R^3$, and $R^5$ each represent independently for each occurrence H or alkyl; $R^4$ and $R^6$ are H; $R^7$ is chloride; $R^8$ is H; m represents independently for each occurrence 0 or 1.

In certain embodiments, the present invention relates to compound II, wherein M is Cu, Co, Fe, Ni, Zn, Ru, or Rh.

In certain embodiments, the present invention relates to compound Ia, wherein M is Cu, Co, Ru, or Rh.

In certain embodiments, the present invention relates to compound IIa, wherein M is Cu.

In certain embodiments, the present invention relates to compound Ia, wherein L is halogen, alkoxy, —OC(O)alkyl, —OC(O)aryl, or —OC(O)aralkyl.

In certain embodiments, the present invention relates to compound Ia, wherein L is halogen.

IV. FLUORESCENCE ASSAYS (A) Instrumentation

Fluorescence of a sensor provided by the present invention may be detected by essentially any suitable fluorescence detection device. Such devices are typically comprised of a light source for excitation of the fluorophore and a sensor for detecting emitted light. In addition, fluorescence detection devices typically contain a means for controlling the wavelength of the excitation light and a means for controlling the wavelength of light detected by the sensor. Such means for controlling wavelengths are referred to generically as filters and can include diffraction gratings, dichroic mirrors, or filters. Examples of suitable devices include fluorimeters, spectrofluorimeters and fluorescence microscopes. Many such devices are commercially available from companies such as Hitachi, Nikon, Molecular Dynamics or Zeiss. In certain embodiments, the device is coupled to a signal amplifier and a computer for data processing.

(B) General Aspects

In general, assays using sensors provided by the present invention involve contacting a sample with such a sensor and measuring fluorescence. The presence of a ligand that interacts with the sensor may alter fluorescence of the sensor in many different ways. Essentially any change in fluorescence caused by the ligand may be used to determine the presence of the ligand and, optionally, the concentration of the ligand in the sample.

The change may take one or more of several forms, including a change in excitation or emission spectra, or a change in the intensity of the fluorescence and/or quantum yield. These changes may be either in the positive or negative direction and may be of a range of magnitudes, which preferably will be detectable as described below.

The excitation spectrum is the wavelengths of light capable of causing the sensor to fluoresce. To determine the excitation spectrum for a sensor in a sample, different wavelengths of light are tested sequentially for their abilities to excite the sample. For each excitation wavelength tested, emitted light is measured. Emitted light may be measured across an interval of wavelengths (for example, from 450 to 700 nm) or emitted light may be measured as a total of all light with wavelengths above a certain threshold (for example, wavelengths greater than 500 nm). A profile is produced of the emitted light produced in response to each tested excitation wavelength, and the point of maximum emitted light can be referred to as the maximum excitation wavelength. A change in this maximum excitation wavelength, or a change in the shape of the profile caused by ligand in a sample may be used as the basis for determining the presence, and optionally, the concentration of metal in the sample. Alternatively, the emission spectrum may be determined by examining the spectra of emitted light in response to excitation with a particular wavelength (or interval of wavelengths). A profile of emissions at different wavelengths is created and the wavelength at which emission is maximal is called the maximum emission wavelength. Changes in the maximum emission wavelength or the shape of the profile that are caused by the presence of a ligand in a sample may be used to determine the presence or concentration of the ligand in the sample. Changes in excitation or emission spectra may be measured as ratios of two wavelengths. A range of changes are possible, from about a few nms to 5, 10, 15, 25, 50, 75 100 or more nms.

Quantum yield may be obtained by comparison of the integrated area of the corrected emission spectrum of the sample with that of a reference solution. A preferred reference solution is a solution of fluorescein in 0.1 N NaOH, quantum efficiency 0.95. The concentration of the reference is adjusted to match the absorbance of the test sample. The quantum yields may be calculated using the following equation.

$$\Phi_{sample} = \Phi_{standard} \times \frac{\int emission_{sample}}{\int emission_{standard}} \times \frac{Abs_{standard}}{Abs_{sample}}$$

A change in quantum yield caused by a ligand may be used as the basis for detecting the presence of the ligand in a sample and may optionally be used to determine the concentration of the ligand. A range of changes are possible in the subject invention. For example, the difference in the quantum yield for a subject sensor in the presence of a ligand may be about 10%, 25%, 50%, 75% the quantum yield, or it may be 2, 3, 5, 10, 100, 200, 1000, 10000 times greater or more. The same values may be used to describe changes observed in intensity in such the subject assays.

It is expected that some samples will contain compounds that compete with the sensor for the ligand. In such cases, the fluorescence measurement will reflect this competition. In one variation, the fluorescence may be used to determine the presence or concentration of one or more such ligand-competing compounds in a sample.

(C) In Vitro Assays

In one variation, the presence of an analyte in a sample is detected by contacting the sample with a sensor that is sensitive to the presence of the analyte. The fluorescence of the solution is then determined using one of the above-described devices, preferably a spectrofluorimeter. Optionally, the fluorescence of the solution may be compared against a set of standard solutions containing known quantities of the ligand, i.e. the analyte. Comparison to standards may be used to calculate the concentration of the analyte, i.e., the ligand.

The ligand may be any substance described above. The concentration of the ligand may change over time and the fluorescent signal of the sensor may serve to monitor those changes. For example, the particular form of the ligand that interacts with the sensor may be produced or consumed by a reaction occurring in the solution, in which case the fluorescence signal may be used to monitor reaction kinetics.

In certain embodiments, the sample is a biological fluid, lysate, homogenate or extract. The sample may also be an environmental sample such as a water sample, soil sample, soil leachate or sediment sample. The sample may be a biochemical reaction mixture containing at least one protein capable of binding to or altering a metal. Samples may have a pH of about 5, 6, 7, 8, 9, 10, 11, 12 or higher.

(D) In Vivo Assays

In another variation, the presence of a ligand in a biological sample may be determined using a fluorescence microscope and the subject sensors. The biological sample is contacted with the sensor and fluorescence is visualized using appropriate magnification, excitation wavelengths and emission wavelengths. In order to observe co-localization of multiple analytes, the sample may be contacted with multiple sensors simultaneously. In certain embodiments the multiple sensors differ in their emission and/or excitation wavelengths.

Biological samples may include bacterial or eukaryotic cells, tissue samples, lysates, or fluids from a living organism. In certain embodiments, the eukaryotic cells are nerve cells, particularly glutamate neurons. In other embodiments, the eukaryotic cells are neurons with mossy fiber terminals isolated from the hippocampus. Tissue samples are preferably sections of the peripheral or central nervous systems, and in particular, sections of the hippocampus containing mossy fiber terminals. It is also anticipated that the detection of a ligand in a cell may include detection of the ligand in subcellular or extracellular compartments or organelles. Such subcellular organelles and compartments include: Golgi networks and vesicles, pre-synaptic vesicles, lysosomes, vacuoles, nuclei, chromatin, mitochondria, chloroplasts, endoplasmic reticulum, coated vesicles (including clathrin coated vesicles), caveolae, periplasmic space and extracellular matrices.

(E) Assays Using a Nitric Oxide Sensor of the Present Invention

In certain embodiments of the above assays, the sensor is an NO sensor and the ligand is NO. The solution or biological sample is contacted with an NO sensor, and fluorescence of the sensor is excited by light with an appropriate wavelength for the fluorophore of the sensor as known to one of skill in the art. Light emitted by the sensor is detected by detecting light of the expected emission wavelength of the fluorophore of the sensor as known to one of skill in the art.

V. METHODS OF USING FLUORESCEIN-BASED LIGANDS

In part, the subject invention is directed to a method of detecting, and optionally quantifying the concentration of, an analyte in a sample, comprising: a) adding to a sample a fluorescein-based sensor of Formula I or Ia, wherein the sample contains a transition metal M; b) measuring the fluorescence of said sensor in said sample; and c) determining whether an analyte is present in said sample. In certain embodiments, the analyte is nitric oxide.

In part, the subject invention is directed to a method of detecting, and optionally quantifying the concentration of, an analyte in a sample, comprising: a) adding to a sample a fluorescein-based sensor of Formula I or Ia; b) adding a transition metal M to the sample, optionally measure the fluorescence of said sensor in said sample prior to adding M; c) measuring the fluorescence of said sensor in said sample; and d) determining whether an analyte is present in said sample. In certain embodiments, the analyte is nitric oxide.

In part, the subject invention is directed to a method of detecting, and optionally quantifying the concentration of, an analyte in a sample, comprising: a) measuring the fluorescence of a fluorescein-based sensor of Formula II or Ia in a sample; and b) determining whether an analyte is present in said sample. In certain embodiments, the analyte is nitric oxide.

In a further embodiment, said sample is a cell. In a further embodiment, said sample is in vivo. In a further embodiment, the method further comprises measuring the fluorescence of said sensor in said sample at a different concentration of said sensor. In a further embodiment, said analyte is nitric oxide.

In part, the subject invention is directed to a method of detecting, and optionally quantifying the concentration of, a target in a sample, comprising: a) mixing with a sample a fluorescein-based compound of the subject invention; b) measuring the fluorescence of said compound in said sample; and c) determining whether the target is present in said sample, and optionally the concentration of said target in said sample.

V. KITS

This invention also provides kits for conveniently and effectively implementing the methods of this invention. Such kits comprise any subject composition, and a means for facilitating compliance with methods of this invention. Such kits provide a convenient and effective means for assuring that the subject to be treated takes the appropriate active in the correct dosage in the correct manner. The compliance means of such kits includes any means which facilitates administering the actives according to a method of this invention. Such compliance means include instructions, packaging, and dispensing means, and combinations thereof. Kit components may be packaged for either manual or partially or wholly automated practice of the foregoing methods. In other embodiments involving kits, this invention contemplates a kit including compositions of the present invention, and optionally instructions for their use.

In part, the subject invention is directed to a diagnostic kit for nitric oxide, comprising: a) a fluorescein-based ligand of the subject invention; and b) instructions for using said ligand to detect nitric oxide in a sample.

EXEMPLIFICATION

The invention, having been generally described, may be more readily understood by reference to the following examples, which are included merely for purposes of illustration of certain aspects and embodiments of the present invention, and are not intended to limit the invention in any way. All headings are for the convenience of the reader and should not be used to limit the meaning of the text that follows the heading, unless so specified.

Example 1

Synthesis of Copper-Fluorescein Sensors

Figure 2:
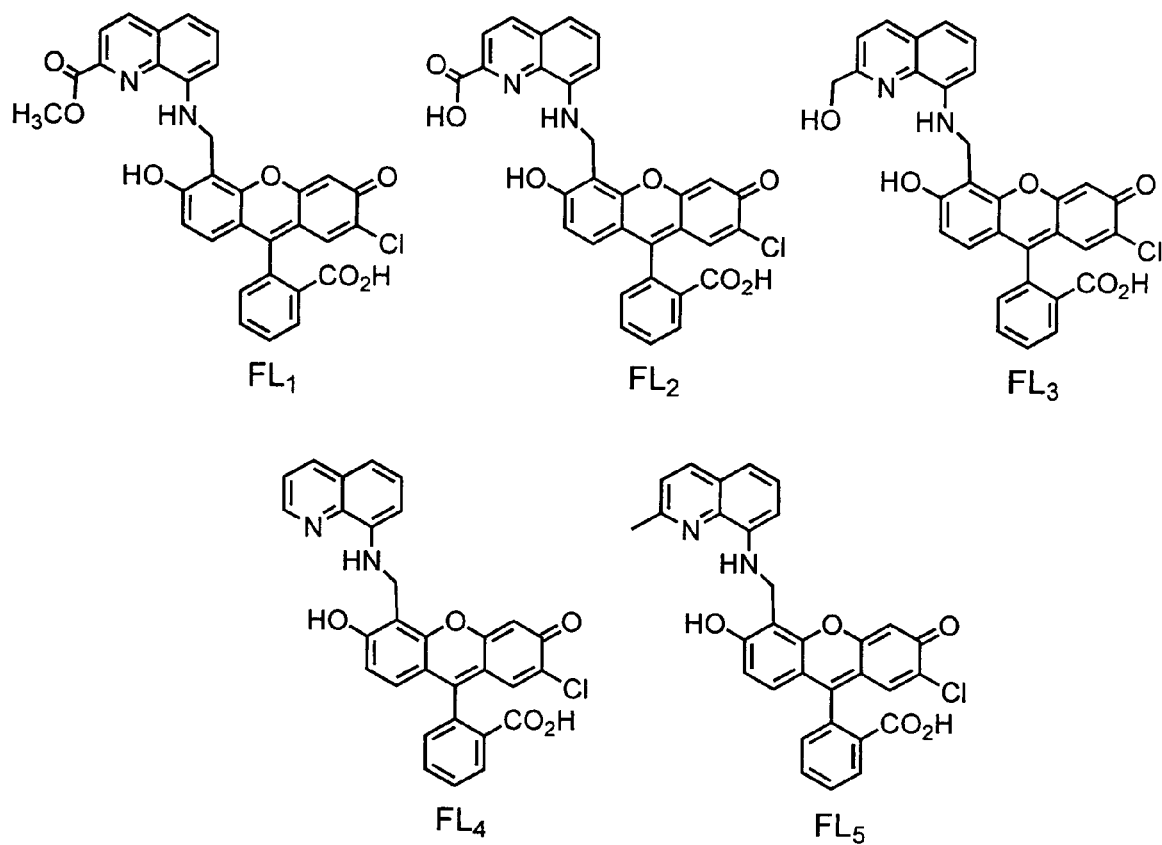
FIG. 2 depicts the structures of the five fluorescein ligands produced in the synthetic strategy of FIG. 1.
Figure 3:
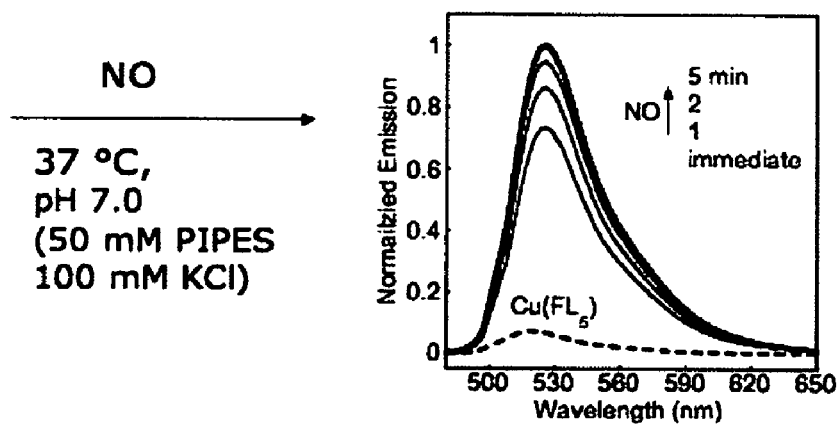
FIG. 3 depicts conditions and results of fluorescence studies on the five sensors of FIG. 2.

FIG. 1 depicts the synthetic strategies for the five fluorescein ligands $FL_n$ (n=1-5).
FIG. 2 depicts the structures of the five fluorescein ligands.
Fluorescence studies of the five sensors are depicted in FIG. 3.

Example 2

Detailed Synthetic Method for Copper-Fluorescein Sensor $Cu(FL_5)$

Derivatized fluorescein molecules are excellent biosensors because they excite and emit in a region of the visible spectrum that is relatively free of interference. We prepared the fluorescein-based ligand $FL_5$ (FIG. 4) by reacting 7'-chloro-4'-fluorescein-carboxaldehyde with 8-aminoquinaldine. We generated the Cu(II) fluorescein-based NO probe $Cu(FL_5)$ (FIG. 4) in situ reacting $FL_5$ (prepared as described below) awith $CuCl_2$ in a 1:1 ratio in buffered aqueous solution (50 mM PIPES, pH 7.0, 100 mM KCl). The Cu(II) species exhibited a blue-shifted $\lambda_{max}$ at 499 nm ($\epsilon=4.0\times10^4$ $M^{-1}cm^{-1}$), compared to that of $FL_5$ (504 nm, $\epsilon=4.2\times10^4$ $M^{-1}cm^{-1}$). A Job's plot was constructed to evaluate the nature of the $FL_5$: Cu(II) complex by following the UV-vis absorption spectral change at 512 nm in pH 7.0 buffered solution. A break at 0.5 indicated the formation of a 1:1 complex. The negative ion electrospray mass spectrum of this species displays a peak with m/z of 632.0 corresponding to $[Cu(FL_5)Cl—H]^-$ (calcd. m/z 632.0). When $FL_5$ was titrated with $CuCl_2$ at 25° C., the absorption changes could be fit to a one-step binding equation with an apparent dissociation constant ($K_d$) of 1.5±0.3 μM for Cu(II) ion.

A. Synthesis of 2-{2-chloro-6-hydroxy-5-[(2-methylquinolin-8-ylamino)-methyl]-3-oxo-3H-xanthen-9-yl}-benzoic acid ($FL_5$). To 2 mL of EtOAc were added 7'-chloro-4'-fluorescein-carboxaldehyde (30 mg, 0.076 mmol) and 8-aminoquinaldine (12 mg, 0.076 mmol). After the reaction was stirred overnight at room temperature, the solvent was removed under reduced pressure. The residue was dissolved in 2 mL of MeOH and the reaction solution was cooled to 0° C. A portion of $NaBH_4$ (14 mg, 0.38 mmol) was added and the reaction solution was stirred at 0° C. for 1 h before being allowed to come slowly to room temperature with stirring overnight. The solvent was removed under reduced pressure and the crude material was purified by preparative TLC on silica gel ($CH_2Cl_2$:MeOH, 20:1 v/v): $R_f$=0.34, affording the FL product as a magenta solid (9 mg, 0.017 mmol, 22%).

B. Synthesis of 2-{2-chloro-6-hydroxy-5-[((2-methylquinolin-8-yl)(nitroso)amino)-methyl]-3-oxo-3H-xanthen-9-yl}-benzoic acid, $FL_5$–NO. Sodium nitrite ($Na^{14}NO_2$ or $Na^{15}NO_2$, 5 mg, 72 μmol, in 100 μL dd $H_2O$) was added to a mixture of $FL_5$ (1.5 mg, 2.8 μmol, in 200 μL $CH_3OH$) and 0.3 M NaOH (aq, 100 μL) on ice. Hydrochloric acid (100 μL, 6 M aq) was slowly introduced to the reaction solution on ice, affording a reddish precipitate. After the solution was centrifuged, LC-MS analyses of both the supernatant and the precipitate, redissolved in $MeOH/H_2O$, were performed. The latter revealed a mixture of $FL_5$–NO and $FL_5$ (data not shown). The supernatant mostly contained the expected product $FL_5$–NO. Excess sodium nitrite was removed from the supernatant by dialysis using a Spectra/Pro® CE (Spectrum®) membrane (MW cutoff 500). An orange solid sample (0.6 mg, 1.1 μmol, 39%) of $FL_5$–NO was obtained by lyophilization and characterized without further purification. TLC (silica, 1:9 $CH_3OH$:$CH_2Cl_2$) showed only one component with $R_f$=0.6.

Example 3

Fluorescence and Mechanistic Studies of $Cu(FL_5)$ with NO

Figure 5:
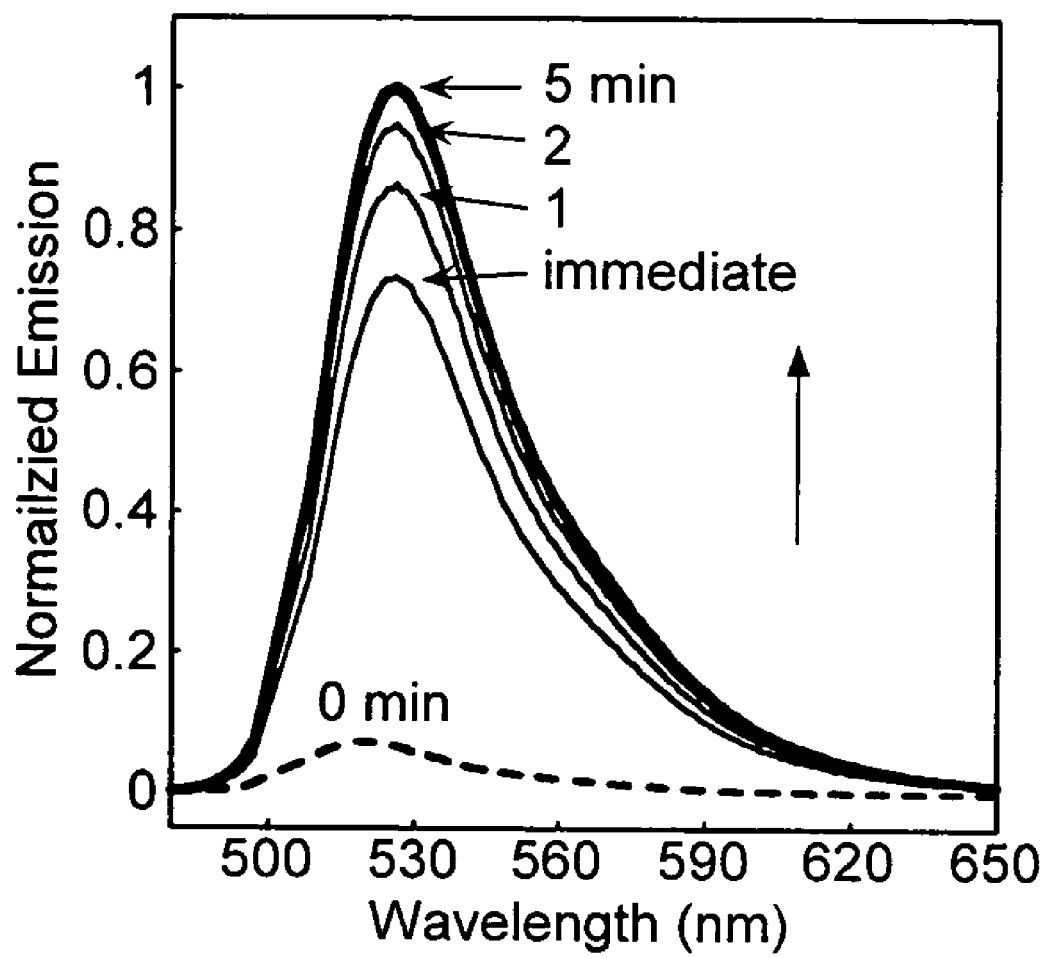
FIG. 5 depicts the fluorescence response of $Cu(FL_5)$ to NO. Fluorescence emission spectra ($\lambda_{ex}$=503 nm) of a deoxygenated 1 µM solution of $Cu(FL_5)$ in buffered solution (50 mM PIPES, pH 7.0, 100 mM KCl) before (dashed line), immediately, 1, 2 and 5 min after (solid lines) admission of 1300 equiv of NO (g) at 37° C.
Figure 6:
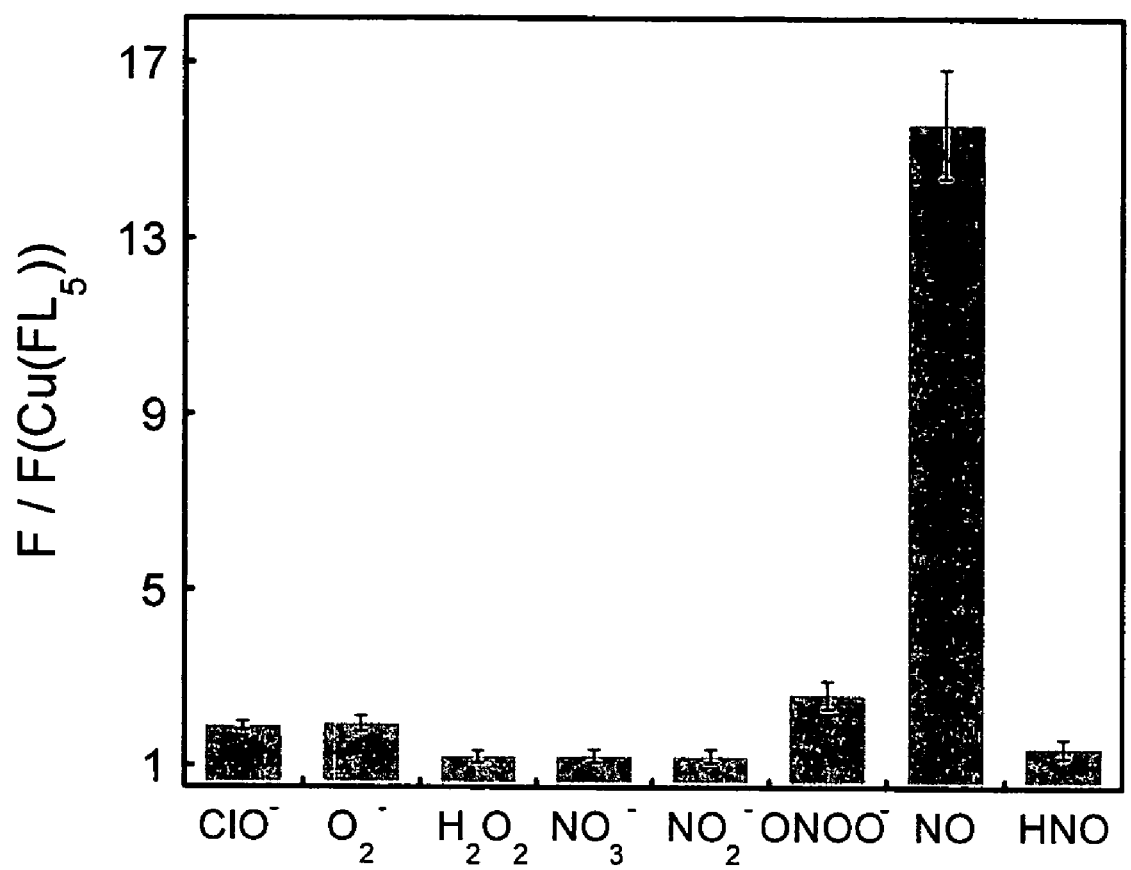
FIG. 6 illustrates the specificity of $Cu(FL_5)$ for NO over other reactive nitrogen and oxygen species. The fluorescence response of $Cu(FL_5)$ was determined after addition of 100 equivalents of $O_2^-$, $ClO^-$, $H_2O_2$, HNO (Angeli's salt $Na_2N_2O_3$), $NO_2^-$, $NO_3^-$, and $ONOO^-$ for 2 h in buffered aqueous solution (50 mM PIPES, pH 7.0, 100 mM KCl). The excitation wavelength was 503 nm. All data (F) are normalized with respect to the emission of $Cu(FL_5)$ ($F(Cu(FL_5))$). [$Cu(FL_5)$]=1 µM. Error bars indicate s.d.

The fluorescence of a 1 μM $FL_5$ solution was diminished by 18±3% upon introduction of an equimolar quantity of $CuCl_2$ at 37° C. Addition of excess NO to a buffered aqueous $Cu(FL_5)$ solution led to an immediate 11.2±1.5-fold increase in fluorescence (FIG. 5). Fluorescence was also enhanced when $Cu(FL_5)$ was allowed to react with the NO-releasing chemical agent S-nitroso-N-acetyl-D,L-penicillamine (SNAP) at pH 7.0 (50 mM PIPES, 100 mM KCl) over a 30 min time interval. This result demonstrates rapid NO detection with significant turn-on emission at a physiologically relevant pH. The lower detection limit for NO is 5 nM. The fluorescence response of the $Cu(FL_5)$ probe detects NO specifically over other reactive species present in biological systems, including $O_2^-$, $ClO^-$, $H_2O_2$, HNO, $NO_2^-$, $NO_3^-$, and $ONOO^-$ (FIG. 6).

A commercially available NO probe, DAF-2 (o-diaminofluorescein), was used for comparison with $Cu(FL_5)$. The fluorescence of DAF-2 is unchanged in the presence of NO and the absence of $O_2$ over a period of 1 h. It only displays turn-on fluorescence when $O_2$ is present, indicating that DAF-2 is incapable of direct NO detection. $Cu(FL_5)$, however, shows an immediate fluorescence response under both anaerobic and aerobic conditions.

In a control experiment, a copper-free $FL_5$ solution treated with excess NO displayed only a small, 1.5±0.2-fold increase in fluorescence over 30 min. In addition, the fluorescence was only marginally increased (1.3±0.2-fold) upon addition of NO to the $Cu(FL_5)$ solution in the presence of excess N,N'-1,2-ethanediylbis-(N-(carboxymethyl)glycine (EDTA), which chelates Cu(II) ion. Both results indicate that the binding of $FL_5$ to Cu(II) is indispensable for fluorescence enhancement by NO.

Figure 4:
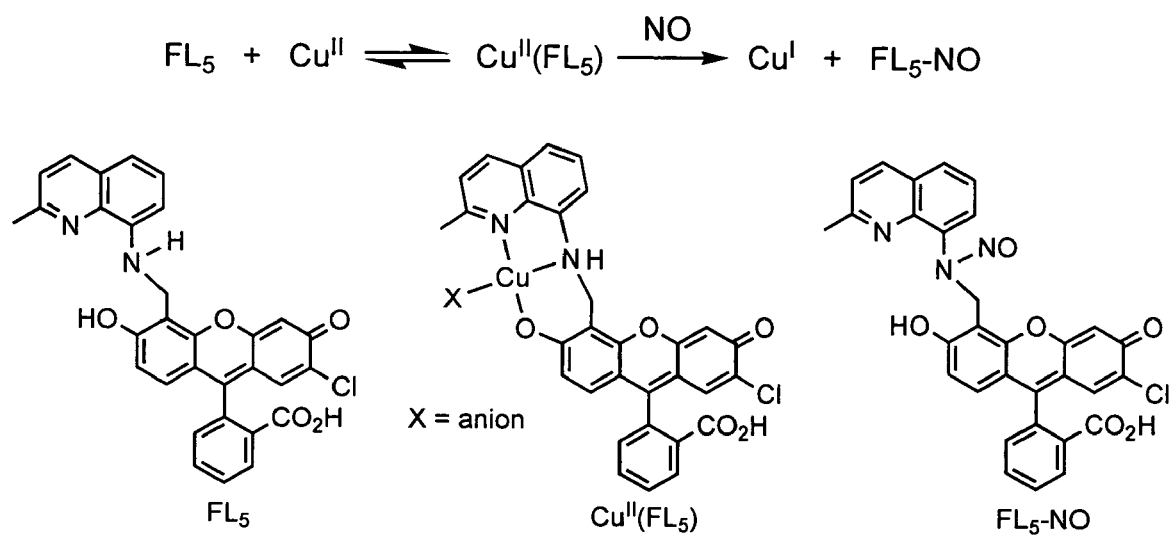
FIG. 4 depicts structures and reaction chemistry of $FL_5$- or "$Cu(FL_5)$".

As depicted in FIG. 4, NO detection by $Cu(FL_5)$ occurs, formally, by nitric oxide-induced reduction of Cu(II) to Cu(I), forming $NO^+$, which nitrosates the ligand with concomitant dissociation from copper and fluorescence turn-on. The mechanism of turn-on emission of $Cu(FL_5)$ by NO was investigated by EPR, UV-vis, NMR and fluorescence spectroscopy and by liquid chromatography-mass spectrometry (LC-MS, low resolution MS). The EPR experiment revealed a 2.9-fold decrease of the axial Cu(II) signal upon $Cu(FL_5)$ reaction with 5 equivalents of NO in DMF, confirming the formation of a Cu(I) species. A mixture of $FL_5$ and $[Cu(CH_3CN)_4](BF_4)$ shows the same fluorescence intensity as that of $FL_5$ and exhibited only a 1.3±0.1-fold increase in fluorescence over 30 min when treated with excess NO. This result indicates that Cu(I)(FL$_5$) is not the species responsible for the fluorescence increase in the NO reaction of Cu(FL$_5$).

LC-MS analyses of the NO reaction product with Cu(FL$_5$) (pH 7.0 buffered aqueous solution) revealed a major peak (93±3%) in the chromatogram with m/z=564.7, 600.5, and 1128.9, masses corresponding to those of [FL$_5$+NO−2H]$^-$ (calcd. m/z 564.1), [FL$_5$+NO−H+Cl]$^-$ (calcd. m/z 600.0), and [2(FL$_5$+NO)−3H]$^-$ (calcd. m/z 1129.2), respectively. This species, which results from nitrosation of the FL$_5$ ligand (FL$_5$−NO, FIG. 4), is stable for several days at pH 7.0, indicating the irreversibility of the NO reaction with Cu(FL$_5$). FL$_5$−NO was independently prepared by the reaction of FL$_5$ with HNO$_2$ and was analyzed by LC-MS, revealing only one LC peak with m/z=564.6, 600.1, and 1129.2 and appearing at the same retention time as that of the reaction product of Cu(FL$_5$) with NO. The electrospray mass spectrum of FL$_5$-$^{15}$NO obtained from a reaction of FL$_5$ with H$_{15}$NO$_2$ exhibited the shifts in m/z (565.8, 601.3, and 1131.2) expected for the Δm/z values of $^{14}$NO vs $^{15}$NO. ESI-MS/MS analysis of the major peaks with m/z=564.6 or 565.8 indicated that a NO functionality is embedded in the final NO reaction product. High resolution MS of FL$_5$-$^{14}$NO and FL-$^{15}$NO were also obtained, showing m/z=600.0729 for FL$_5$-$^{14}$NO and 601.0736 for FL$_5$-$^{15}$NO, corresponding to [FL$_5$+NO−H+Cl]$^-$ (calcd. m/z 600.0729 and 601.0700).

Upon addition of excess NO, a 499 nm peak in the UV-vis spectrum of Cu(FL$_5$) in pH 7.0 buffered solution red-shifted back to the λ$_{max}$ characteristic of FL$_5$ or the synthetic FL$_5$−NO compound (504 nm), which differs from the band formed in the reaction of FL$_5$ with 1 equivalent of Cu(I) added as [Cu(CH$_3$CN)$_4$](BF$_4$) (506 nm). This result indicates that the nitrosation reaction may occur at the metal binding site, which has one oxygen and two nitrogen donor atoms, releasing the nitrosated ligand from the copper center. The optical spectrum of the reaction of a pH 7.0 solution of Cu(FL$_5$) with NO exhibited the same features as that of the dianionic form of FL$_5$ at pH 7.0. In addition, the spectrum of the NO reaction solution closely resembled that of the monoanionic fluorescein formed by lowering the pH from 7.0 to 5.0. These spectroscopic observations are consistent with those of fluorescein, the properties of which vary with pH, and strongly imply that FL$_5$ nitrosation does not occur at a hydroxyl group on the xanthene ring. To pinpoint the position of FL$_5$ nitrosation, an 15N NMR spectrum of FL$_5$-$^{15}$NO was recorded, revealing 15N chemical shifts at 167.33 and 169.61 ppm vs CH$_3$NO$_2$ in a relative ratio of 7:3. These values are in the range previously reported for N-nitrosamines. The presence of two separate chemical shifts might arise from different isomers in solution, the Δδ of 2.29 being similar to that of previously reported of N-nitrosamines. A $^1$H NMR spectrum of the isolated FL$_5$−NO molecule also revealed the presence of a 7:3 isomeric mixture. Both the 15N chemical shift values and the existence of isomers in the $^{15}$N NMR spectrum of FL$_5$−NO clearly demonstrate that FL$_5$ is N-nitrosated at the secondary amine functionality, as illustrated in FIG. 4. Lastly, FL$_5$−NO is brighter than FL$_5$ or Cu(FL$_5$), the respective quantum yields being Φ$_{FL-NO}$=0.58±0.02 and Φ$_{FL}$=0.077±0.002.

Taken together, these results demonstrate that Cu(FL$_5$) is capable of fluorescent NO detection via NO-induced metal reduction followed by the release of the nitrosated ligand from copper with concomitant fluorescence enhancement (FIG. 4). Formation of an N-nitrosamine was previously observed in the reaction of NO with a Cu(II) complex containing two anthracene groups as light-emitting units in aqueous methanol solution with fluorescence turn-on over 46 min. Other copper fluorophore complexes have been reported as fluorescent NO indicators and similarly operate via reduction of Cu(II) to Cu(I) by NO.

Example 4

Cu(FL$_5$) Detection of NO Produced by cNOS

We investigated the ability of Cu(FL$_5$) to detect NO produced in SK-N-SH human neuroblastoma cells under physiological conditions, since constitutive NO synthase ("cNOS") in this cell line can be activated by estrogen to produce NO. Estrogen administration leads to an increase in the cytosolic Ca(II) concentration that alters the structure of calmodulin, which in turn activates cNOS. The NO-dependent fluorescence response, monitored after simultaneous administration of 17β-estradiol (100 nM) and Cu(FL$_5$) (1 µM) to the cells, was completed within 5 min with a 4.0±0.6-fold increase in fluorescence (FIGS. 5a and b). We also demonstrated an increase in cytosolic Ca(II) levels following addition of 17β-estradiol to SK-N-SH cells using the calcium dye fluo-4 AM, which is consistent with estrogen induction of Ca(II)-dependent NO production. A notably weaker fluorescence response was observed in the presence of the cNOS inhibitor N$^G$-nitro-L-arginine (L-NNA), pinpointing nitric oxide to be responsible for the fluorescence change (FIG. 5c). In a control experiment, stimulated SK-N-SH cells incubated with FL$_5$ in the absence of Cu(II) ion exhibited no fluorescence increase over a period of 25 min. This result demonstrates that Cu(FL$_5$), but not FL$_5$, is responsible for the fluorescence change. As another control, HeLa cells were co-treated with 17β-estradiol (100 nM) and Cu(FL$_5$) (1 µM). The absence of turn-on emission in these cells indicates that the fluorescence response of Cu(FL$_5$) is not a consequence of its interaction with 17β-estradiol.

The value of Cu(FL$_5$) as a probe for NO-related research has been further demonstrated by comparing its ability to image NO in cells with that of a commercially available sensor DAF-2 DA (o-diaminofluorescein diacetate). Firstly, Cu(FL$_5$) visualizes NO in the estradiol-stimulated neuroblastoma cells with brighter fluorescence than DAF-2 DA (o-diaminofluorescein diacetate). In addition, there was only a slight fluorescence increase of DAF-2 DA-treated cells 30 min after activation of cNOS, whereas Cu(FL$_5$) provided complete fluorescence enhancement within 5 min (FIG. 5). These results reveal that Cu(FL$_5$) allows fast and direct visualization of NO in live cells.

Example 5

Cu(FL$_5$) Detection of NO Produced by iNOS

In macrophages, nitric oxide is produced by inducible NO synthases ("iNOS"). Time-dependent NO production by Raw 264.7 cells pretreated with bacterial lipopolysaccharide (LPS) and interferon-γ (IFN-γ) has been previously demonstrated by using the Griess assay. This method colorimetrically determines the concentration of NO$_2^-$ resulting from NO oxidation in the extracellular space. Fluorescence detection of NO production by stimulated macrophage cells was also achieved by incubation of the extracellular fluid with DAN and DAFs. These dyes improved the sensitivity of Griess assay, but were unable to reveal NO production inside cells with spatial and temporal fidelity. The present Cu(FL$_5$) construct, however, readily detects NO produced in activated Raw 264.7 cells by fluorescence turn-on. Macrophage cells were incubated with LPS (500 ng/mL) and IFN-γ (250 U/mL)

for 4 h, after which 1 μM Cu(FL$_5$) was applied. The fluorescence response was monitored at 2 h intervals by microscopy (FIG. 6a). The average fluorescence slowly increased over 12 h in almost every region of the treated cells.

The production of nitric oxide in LPS- and IFN-γ treated macrophages was independently confirmed by the Griess assay, which revealed identical kinetics of NO formation inside and outside the cells over the 12 h period of the experiment. To investigate further the origin of fluorescence detected by Cu(FL$_5$), iNOS was silenced in Raw 264.7 cells by short hairpin RNA (shRNA)-induced RNA interference (RNAi) (FIG. 6b). Upon stimulation by LPS and IFN-γ, the cells with iNOS attenuated displayed a much weaker fluorescence response than those harboring only the plasmid vector (FIG. 6c), clearly demonstrating that the fluorescence enhancement is caused by nitric oxide production in Raw 264.7 cells. In addition, a notably weaker fluorescence response was observed for stimulated Raw 264.7 cells in the presence of N$^G$-methyl-L-arginine (L-NMA), a known inhibitor of iNOS that attenuates NO production, than in its absence. As a control experiment, turn-on fluorescence emission was not observed after FL$_5$ treatment without Cu(II) ion for Raw 264.7 cells stimulated by LPS and IFN-γ over the 12 h incubation period and for HeLa cells treated with LPS and IFN-γ prior to Cu(FL$_5$) incubation.

Example 6

NO Imaging in a Raw 264.7 and SK-N-SH Co-Culture

Figure 9:
FIG. 9 illustrates NO detection in SK-N-SH and Raw 264.7 cells by $Cu(FL_5)$. Cells were treated with $Cu(FL_5)$ (1 µM) and 17β-estradiol (500 nM) for 10 min. The media were subsequently removed and the cells washed with PBS. Images were taken with a Nikon Eclipse TS100 microscope.

The fluorescence response was also monitored in a mixture of Raw 264.7 and SK-N-SH cells grown on the same plate and co-treated with 17β-estradiol (100 nM) and Cu(FL$_5$) (1 μM) for 10 min. As shown in FIG. 9, a fluorescence increase was observed exclusively in the SK-N-SH cells following cNOS activation by 17β-estradiol-triggered Ca(II) release into cytosol. This result demonstrates that Cu(FL$_5$) might be used to provide information about which types of cells are producing NO in a heterogeneous tissue, and possibly be useful for identifying the time and location of intercellular signaling events.

Example 7

Cytotoxicity of Cu(FL$_5$) and FL$_5$–NO

To test the toxicity of Cu(FL$_5$), a MTT [3-(4,5-dimethylthiazol-2-yl)-2,5-diphenyltetrazolium bromide] assay was performed on SK-N-SH cells after 5 days of incubation with Cu(FL$_5$) (1 μM). The result [80±9% survival of cells] indicates that the Cu(II)-containing probe is not toxic to SK-N-SH cells under the conditions of NO imaging employed herein.

The MTT assay also indicated 90±3% survival of Raw 264.7 cells after incubation with Cu(FL$_5$) (1 μM) for 5 days, indicating that Cu(FL$_5$) is not toxic to this cell line. Furthermore, Cu(FL$_5$) does not affect the expression of iNOS in Raw 264.7 cells upon introduction of LPS and IFN-γ, which suggests that the concentration of Cu(FL$_5$) used for imaging does not interrupt the biological pathways required for NO production via gene expression.

Lastly, the toxicity of FL$_5$–NO, the product of the reaction of Cu(FL$_5$) with NO, was examined in SK-N-SH cells by the MTT assay, which revealed 97±2% cell survival after 5 days. Thus, both Cu(FL$_5$) and FL$_5$–NO are not toxic under the conditions used here for bioimaging of NO.

Example 8

Cell Cultures and Assays

Raw 264.7, SK-N-SH, and HeLa cells were purchased from the American Type Culture Collection (ATCC). All three cell lines were maintained in Dulbecco's modified Eagles' media (DMEM) (GibcoBRL) containing 10% (v/v) heat-inactivated fetal bovine serum (FBS) (HyClone), 1 mM sodium pyruvate (Sigma), 100 units/ml penicillin, 100 μg/ml streptomycin (Invitrogen), and 0.1 mM nonessential amino acid solution for minimal essential medium (Sigma). All cells were grown at 37° C. in a humidified atmosphere of 10% CO$_2$. A nitrite assay was performed with Griess reagents (Promega) on Raw 264.7 cells grown in DMEM free of phenol red. Calcium sensor fluo-4 AM was purchased from Invitrogen. MTT [3-(4,5-dimethylthiazol-2-yl)-2,5-diphenyltetrazolium bromide] (Sigma-Aldrich) assay was described in Supplementary information. The expression of iNOS in Raw 264.7 cells was analyzed by Western blot on the extracts of cells stimulated by LPS and INF-γ. The protein was silenced by short hairpin RNA-induced RNAi and the resulting cell lines were used in fluorescence imaging by Cu(FL$_5$).

Example 9

Discussion of Examples 2-8

We have devised an imaging agent to detect NO directly in vitro at neutral pH as well as in live cells. The probe is a Cu(II) complex Cu(FL$_5$) (FIG. 4) containing a fluorescein-based ligand that provides suitable excitation and emission wavelengths as well as brightness for NO bioimaging. This Cu(II)-based compound directly captures NO in a reaction that generates Cu(I) and NO$^+$. The latter reacts irreversibly with the fluorescein-based ligand FL$_5$, which is nitrosated and released from copper with significant turn-on fluorescence (FIG. 4, FIG. 5). This mechanism was proved by detailed spectroscopic, magnetic, and mass spectrometric measurements. A comparison of Cu(FL$_5$) with DAF-2 (FIG. 5) clearly reveals that only Cu(FL$_5$) can directly detect NO with fluorescence turn-on in the absence of oxygen. The ability of Cu(FL$_5$) to image NO specifically over other reactive nitrogen or oxygen species in living organisms (FIG. 6), such as $O_2^-$, $ClO^-$, HNO, $NO_2^-$, $NO_3^-$, $ONOO^-$, and $H_2O_2$, increases its value for a wide range of biological studies. To our knowledge, Cu(FL$_5$) is the first probe capable of direct, fast and specific NO detection.

Figure 7:
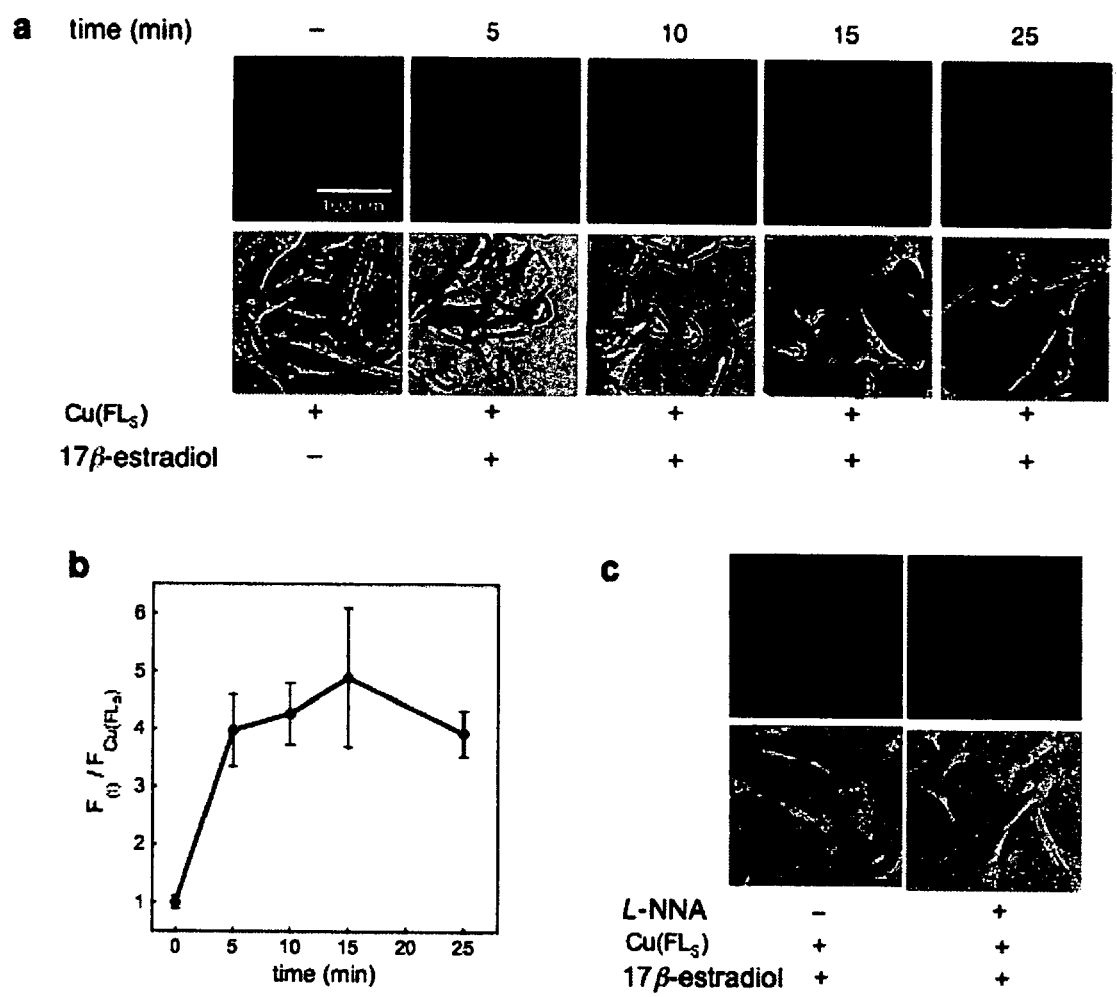
FIG. 7 illustrates $Cu(FL_5)$ detection of NO produced by cNOS. (a) NO detection in SK-N-SH cells by $Cu(FL_5)$. Left to right: 25 min incubation of $Cu(FL_5)$ (1 µM) and 5, 10, 15, 25 min after co-treatment of $Cu(FL_5)$ (1 µM) and 17β-estradiol (100 nM). Images were taken with a Nikon Eclipse TS100 microscope after removing the DMEM media and washing the cells with PBS. Top: fluorescence images; bottom: phase contrast images. (b) Fluorescence intensity ($F_{(t)}$/$F_{Cu(FL5)}$) from a was plotted against incubation time. (c) NO production with or without of L-NNA. Right: NO detection in cells after 10 min co-incubation of $Cu(FL_5)$ (1 µM) and 17β-estradiol (100 nM). Left: NO detection in cells pre-treated with L-NNA for 1 h before addition of $Cu(FL_5)$ and 17β-estradiol.
Figure 8:
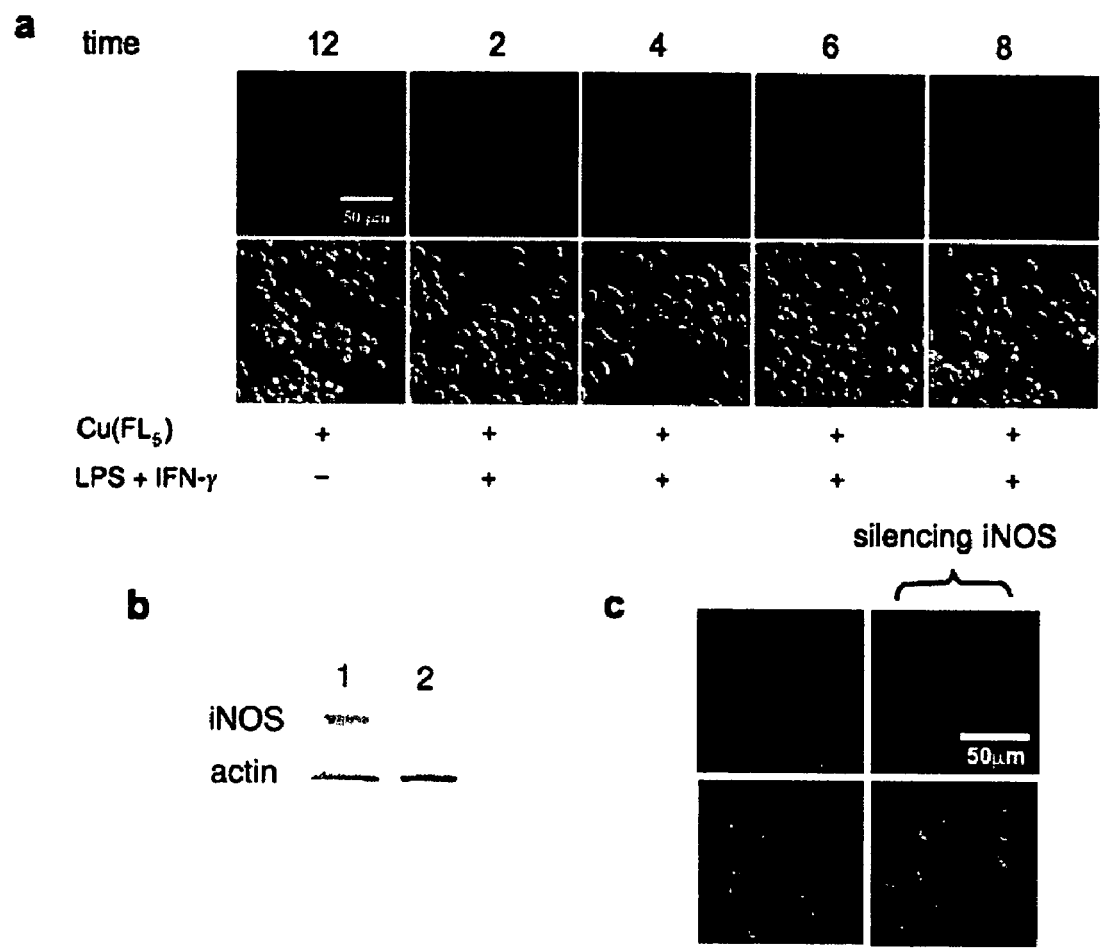
FIG. 8 illustrates $Cu(FL_5)$ detection of NO produced by iNOS. (a) NO detection in Raw 264.7 macrophage cells by $Cu(FL_5)$. Left to right: $Cu(FL_5)$ (1 µM) incubation with cells for 12 h, and 2, 4, 6, 8 h after addition of $Cu(FL_5)$ into cells that were pre-stimulated for 4 h with LPS (500 ng $mL^{-1}$) and IFN-γ (250 U $mL^{-1}$). The times depicted in the figure are the total incubation times with $Cu(FL_5)$. Images were taken immediately after removing the media and washing the cells three times with PBS. The instrument used was a Zeiss Axiovert 200M inverted epifluorescence microscope with differential interference contrast (DIC). Top: fluorescence images; bottom: DIC images. (b) Silencing of iNOS by RNAi in Raw 264.7 cells. A plasmid expressing shRNA was constructed to target the mRNA of iNOS. It was transfected into cells. The plasmid vector without insert for RNAi was transfected to establish a control cell line. The expression of iNOS in these two cell lines after stimulated by LPS and IFN-γ for 12 h was investigated by Western blot on the whole cell extracts with antibodies against the protein and actin, which served as loading control (lane 1: cells with control plasmid vector, lane 2: cells with plasmid expressing shRNA for iNOS). (c) NO detection in Raw 264.7 cells with iNOS silenced by RNAi. The two lines in (b) were treated with LPS and IFN-γ for 4 h before 8 h of incubation with $Cu(FL_5)$.

In mammalian cells, nitric oxide is produced by three isoforms of NO synthase (NOS): neuronal NOS (nNOS), endothelial NOS (eNOS) and inducible NOS (iNOS), the catalytic activities of which are well-studied. Functionally, NOS can be categorized as cNOS or iNOS. cNOS, including nNOS and eNOS, is regulated by the cytosolic calcium concentration and produces physiological quantities of NO. The Ca(II)-independent iNOS that provides the pathophysiological concentrations of NO is controlled by gene transcription. We applied Cu(FL$_5$) to image NO production in Raw 264.7 murine macrophage and SK-N-SH human neuroblastoma cells (FIGS. 7, 8). Our studies in both cell lines demonstrate that Cu(FL$_5$) affords direct visual detection of NO production in a time- and concentration-dependent manner from both cNOS and iNOS in living cells with >4-fold fluorescence enhancement and spatial resolution at a cellular level. Cell-type specific fluorescent NO imaging in a co-culture of the two cell lines reveals that Cu(FL$_5$) is capable of detecting a source of nitric oxide production in a complex and heterogeneous biological system (FIG. 9).

Solution and live cell studies (FIGS. 5, 7, 8) clearly demonstrate that $Cu(FL_5)$ is the species responsible for NO detection with fluorescence turn-on. Since the $K_d$ of $Cu(FL_5)$ is 1.5 µM in 50 mM PIPES, pH 7.0, 100 mM KCl, however, the intensity of the observed signal might reflect both the degree of $Cu(FL_5)$ integrity and the amount of NO produced in the cells. Since the concentrations of $FL_5$, Cu(II), and $Cu(FL_5)$ inside cells have yet to be quantified, we cannot presently delineate how these two variables affect the intracellular fluorescence signal. A comparison of NO sensing by $Cu(FL_5)$ vs the commonly used DAF-2 DA reagent, however, reveals that $Cu(FL_5)$ provides rapid NO production with bright fluorescence signals in live cells, which is a significant improvement over this and other organic molecule-based NO probes.

Since the N-nitrosamine $FL_5$–NO generated by the chemistry of $Cu(FL_5)$ in nitric oxide detection is a member of a class of reactive molecules, we investigated its potential cytotoxicity. An MTT assay indicates that it is not toxic at the concentration required for NO imaging in the present studies, since 97±2% of SK-N-SH cells treated with $FL_5$–NO for 5 days survived. Another potential problem is that the copper ion in this $Cu(FL_5)$ might damage cells before or following its reaction with NO. In order to address this possibility, we performed an MTT cytotoxicity assay on cells treated with 1 µM $Cu(FL_5)$, which indicated them to be largely viable (>80%) after 5 days. Thus, under the conditions used for the present NO bioimaging experiments, the toxicity of $Cu(FL_5)$ is negligible.

The cytosol contains thiols that bind Cu(II) and possibly convert it to Cu(I), a species that might itself react with oxidized NO products such as $NO^+$ or $N_2O_3$. Since $NO^+$ is rapidly hydrolyzed to $NO_2^-$ in water, it will not interfere with NO imaging by $Cu(FL_5)$. S-nitrosothiols, formed by reactions of thiols with NO in the presence of $O_2$, react with both $Cu(II)(FL_5)$ and $Cu(I)(FL_5)$ to display turn-on fluorescence as demonstrated in experiments with SNAP. At present we cannot completely rule out the possibility that the fluorescence increase results from reaction of $Cu(FL_5)$ with S-nitrosothiols produced by NO in the stimulated cells. Finally, reduction of Cu(II) by thiols may not alter the integrity or otherwise disrupt the NO-imaging ability of $Cu(FL_5)$ in cells. Cu(II) binding to $FL_5$ is necessary for fluorescence turn-on by NO. Moreover, a mixture of $FL_5$ and Cu(I) does not lead to a fluorescence increase either in the presence or absence of NO, compared to $FL_5$ alone. These experiments strongly support the conclusion that the turn-on fluorescence in the stimulated cells results from the direct reaction of $Cu(FL_5)$ with NO and that intracellular thiols do not interfere with this chemistry.

In summary, we have synthesized a Cu(II)-based fluorescein compound $Cu(FL_5)$ for imaging NO based on redox chemistry. Reduction of $Cu(FL_5)$ by NO to Cu(I) with nitrosation of the $FL_5$ ligand is accompanied by bright visible light emission. The probe readily passes through cell membranes and can detect NO under physiological conditions. Studies of $Cu(FL_5)$ in pH 7.0 aqueous buffered solutions indicate that the NO response is direct, rapid, and specific. Application of $Cu(FL_5)$ to cultures of macrophage and neuroblastoma cells reveals the time-dependent production of NO measurable by fluorescence enhancement, demonstrating the ability of the reagent to image NO over a wide range of concentrations. The power of $Cu(FL_5)$ is also manifest in its ability to select out cells that emit NO in a background of those that do not with spatiotemporal resolution at a cellular level.

These results will encourage the use of $Cu(FL_5)$ as a direct nitric oxide probe for investigating NO biology in a variety of contexts.

REFERENCES

All publications and patents mentioned herein, including those items listed below, are hereby incorporated by reference in their entirety as if each individual publication or patent was specifically and individually incorporated by reference. In case of conflict, the present application, including any definitions herein, will control.

Ignarro, et al. *Proc. Natl. Acad. USA* 1987, 84:9265-9269.
Palmer, et al. *Nature* 1987, 327:524-526.
Wink, et al. *Carcinogenesis,* 1998, 99:711-721.
Moncada, et al. *Pharmacol. Rev.* 1991, 43:109-142.
Kerwin, et al. *J. Med. Chem.* 1995, 38:4343-4362.
Feldman, et al. *J. Chem. Eng. News* 1993, 71:26-38.
Bredt, et al. *Annu. Rev. Biochem.* 1994, 63:175-195.
Butler, et al. *Chem. Soc. Rev.* 1993, 233-241.
Rubbo, et al. *Chem. Res. Toxicol.* 1996, 9:809-820.
Pfeiffer, et al. *Angew. Chem. Int. Ed.* 1999, 38:1714-1731.
Jia, et al. *Nature* 1996, 380:221-226.
Bredt, et al. *Nature* 1990, 347:768-770.
Leone, et al. *J. Biol. Chem.* 1991, 228:23780-23795.
Crane, et al. *Science* 1998, 279:2121-2126.
Marietta, et al. *J. Biol. Chem.* 1993, 266:12231-12234.
Korth, et al. *J. Biol. Chem.* 1994, 269:17776-17779.
Griffith, et al. *Annu. Rev. Physiol.* 1995, 57:707-736.
Laval, et al. *Carcinogenesis,* 1994, 15:443-447.
Calabrese, et al. *Neurochem. Res.* 2000, 25:1315-1341.
Schmidt, et al. In *Methods in Nitric Oxide Research*; Feelish, M, Stamler. J. S., Ed.; John Wiley & Sons: New York, 1996, pp 491-497.
Hampl, et al. In *Methods in Nitric Oxide Research*; Feelish, M., Stamler. J. S., Ed.; John Wiley & Sons: New York, 1996, pp 309-318.
Mao, et al. *Anal. Lett.* 1998, 31:1991-2007.
Bedioui, et al. *Electroanalysis* 2003, 15:5-18.
Ciszewski, et al. *Talanta* 2003, 61:11-26.
Wiersma, et al. *Anal. Lett.* 1970, 3:123-132.
Kojima, et al. *Biol. Pharm. Bull.* 1997, 20:1229-1232.
Kojima, et al. *Anal. Chem.* 1998, 70:2446-2453.
Platter, et al. *J. Chem. Soc. Perkin Trans.* 1, 2001, 2553-2559.
Zhang, et al. *Anal. Chim. Acta* 2003, 481:101-106.
Meineke, et al. *Chem. Eur. J.* 1999, 5:1738-1747.
Batz, et al. *Angew. Chem. Int. Ed.* 1997, 36:1501-1503.
Katayama, et al. *Anal. Chim. Acta* 1998, 385:159-187.
Soh, et al. *Chem. Commun.* 2002, 2650-2651.
Katayama, et al. *Chem. Lett.* 2000, 1152-1153.
Hilderbrand, et al. *Inorg. Chem.* 2004, 43:5294-5301.
Franz, et al. *Inorg. Chem.* 2000, 30:4081-4092.
Hilderbrand, et al. *Inorg. Chem.* 2004, 43:4674-4682.
Lim, et al. *Inorg. Chem.* 2004, 43:6366-6370.
Hilderbrand, et al. *J. Am. Chem. Soc.* 2004, 126:4972-4978.
Nolan, et al. *J. Am. Chem. Soc.* 2005, 127: 16812-16823
Murad, F. *Angew. Chem. Int. Ed.* 1999, 38:1856-1868.
Furchgott, R. F. *Angew. Chem. Int. Ed.* 1999, 38:1870-1880.
Ignarro, L. J. *Angew. Chem. Int. Ed.* 1999, 38:1882-1892.
Packer, L. *Methods in Enzymology, Nitric Oxide. Part B, Physiological and Pathological Processes* (Academic Press, San Diego, Calif., 1996).

Moncada, S., Palmer, R. M. J. & Higgs, E. A. *Nitric oxide: physiology, pathphysiology, and pharmacology. Pharmacol. Rev.* 1991, 43:109-142.

Ricciardolo, et al. *Physiol. Rev.* 2004, 84:731-765.

Conner, E. M & Grisham, M B. *Methods Enzymol.* 1995, 7:3-13.

Nagano, T & Yoshimura, T. *Chem. Rev.* 2002, 102:1235-1269.

Malinski, et al. *Methods Enzymol.* 1996, 268:58-69.

Hilderbrand, S. A., Lim, M. H. & Lippard, S. J. in *Topics in Fluorescence Spectroscopy* (eds. Geddes, C. D. & Lakowicz, J. R.) 163-188 (Springer, 2005).

Sato, et al. *Proc. Natl. Acad. Sci. USA* 2005, 102:14515-14520.

Miles, et al. *Methods Enzymol.* 1995, 7:40-47.

Sasaki, et al. *J. Am. Chem. Soc.* 2005, 127:3684-3685.

Wink, et al. *Methods Enzymol.* 1996, 268:12-31.

Lozinsky, et al. *Anal. Biochem.* 2004, 326:139-145.

Nolan, et al. *Inorg. Chem.* 2004, 43:2624-2635.

Sjöback, et al. *Spectrochim. Acta Part A* 1995, 51:L7-L21.

Bonnett, et al. *J. Chem. Soc. Perkin* 11975, 22:2261-2264.

Karaghiosoff, et al. *J. Org. Chem.* 2006, 71:1295-1305.

Lee, et al. *Chem. Rev.* 2002, 102:1019-1065 and refs cited therein.

Tsuge, et al. *J. Am. Chem. Soc.* 2004, 126:6564-6565.

Lim, M. H. &Lippard, S. J. *J. Am. Chem. Soc.* 2005, 127: 12170-12171.

Smith, et al. *Org. Lett.* 2005, 7:3573-3575.

Xia,Y. & Krukoff, T L. *Endocrinology* 2004, 145:4550-4557.

Marletta, et al. *Curr. Opin. Chem. Biol.* 1998, 2:656-663.

Wang, D. & Lippard, S. J. *J. Biol. Chem.* 2004, 279:20622-20625.

Miwa, et al. *Carcinogenesis* 1987, 8:955-958.

Ralt, et al. *J. Bacteriol.* 1988, 170:359-364.

Ji, X.-B. & Hollocher, T. C. *Appl. Environ. Microbiol.* 1988, 54:1791-1794.

Nakatsubo, et al. *FEBS Lett.* 1998, 427:263-266.

Lijinsky, W. *Chemistry and biology of N-nitroso compounds* (eds. Coombs, M. M., Ashby, J. & Hicks, M.) (Cambridge University Press, Cambridge, 1992).

Koppenol, W. H. *Methods Enzymol.* 1996, 268:7-12.

Ford, P. C. & Lorkovic, L M. *Chem. Rev.* 2002, 102:993-1017.

EQUIVALENTS

Those skilled in the art will recognize, or be able to ascertain using no more than routine experimentation, many equivalents to the specific embodiments of the invention described herein. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations. Such equivalents are intended to be encompassed by the following claims.

We claim:

1. A compound represented by Formula I, comprising:

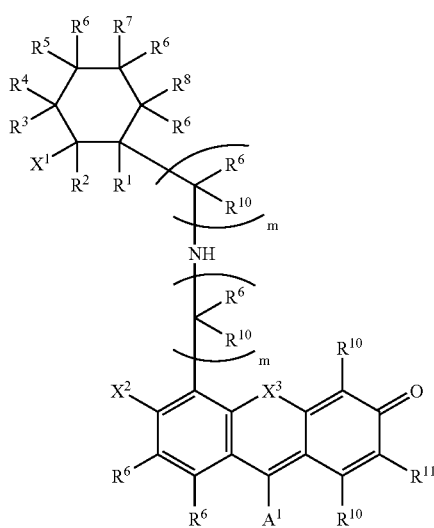

wherein $A^1$ is aryl or heteroaryl, both of which are optionally substituted with one or more of halogen, alkoxyl, —OH, —N($R^{12}$)$_2$, —COR$^{12}$, —CO$_2$R$^{12}$, —N(R$^{12}$)C(O)R$^{12}$, or —C(O)N(R$^{12}$)$_2$;

$X^1$ is —OR$^9$, —SR$^9$, —N=R$^9$, or —N(R$^{13}$)R$^9$;

$X^2$ is —OR$^{13}$, —SR$^{13}$, or —N(R$^{13}$)$_2$;

$X^3$ is —O—, —S—, or —N(R$^{13}$)—;

$R^1$, $R^3$, $R^5$, $R^7$, $R^8$ and $R^{10}$ each represent independently for each occurrence H, alkyl, aryl or heteroaryl; or $R^1$ and $R^8$ taken together form a bond; or $R^5$ and $R^7$ taken together form a bond;

$R^2$, $R^4$, and $R^6$ each represent independently for each occurrence H, alkyl, aryl, heteroaryl, aralkyl, halogen, alkoxyl, —COR$^{12}$, or —CO$_2$R$^{12}$; or $R^2$ and $R^3$ taken together form a bond; or $R^4$ and $R^9$ taken together form a 5-6 member ring optionally substituted with one or more of alkyl, hydroxyalkyl, aryl, aralkyl, halogen, alkoxyl, —N(R$^9$)$_2$, —COR$^9$, —CO$_2$R$^9$, —N(R$^9$)C(O) R$^9$, or —C(O)N(R$^9$)$_2$;

$R^9$ is H, alkyl, aryl, heteroaryl, or aralkyl;

$R^{11}$ is H, alkyl, aryl, heteroaryl, aralkyl, or halogen;

$R^{12}$ represents independently for each occurrence H, alkyl, aryl, heteroaryl, or aralkyl;

$R^{13}$ represents independently for each occurrence H or ($C_1$-$C_6$)alkyl;

m represents independently for each occurrence 0, 1, 2, 3, or 4; and the stereochemical configuration at any stereocenter of a compound represented by I is R, S, or a mixture of these configurations.

2. The compound of claim 1, wherein said compound is represented by Formula Ia:

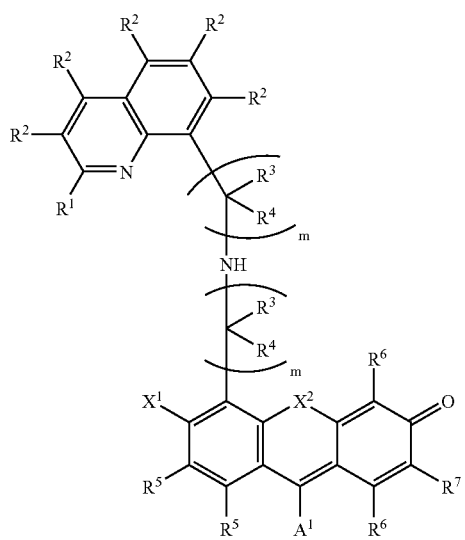

wherein, $A^1$ is aryl or heteroaryl, both of which are optionally substituted with one or more of halogen, alkoxyl, —OH, —$N(R^8)_2$, —$COR^8$, or —$CO_2R^8$;

$X^1$ is —$OR^6$, —$SR^6$, or $N(R^6)_2$;

$X^2$ is —O—, —S—, or —$N(R^6)$—;

$R^1$ represents independently for each occurrence H, alkyl, hydroxyalkyl, aryl, aralkyl, halogen, alkoxyl, —$N(R^8)_2$, —$COR^8$, —$CO_2R^8$, —$N(R^8)C(O)R^8$, or —$C(O)N(R^8)_2$;

$R^2$, $R^3$, and $R^5$ each represent independently for each occurrence H, alkyl, halogen, alkoxyl, —$COR^8$, or —$CO_2R^8$;

$R^4$ and $R^6$ each represent independently for each occurrence H or alkyl;

$R^7$ is halogen;

$R^8$ represents independently for each occurrence H, alkyl, aryl, heteroaryl, or aralkyl;

m represents independently for each occurrence 0, 1, or 2; and the stereochemical configuration at any stereocenter of a compound represented by Ia is R, S, or a mixture of these configurations.

3. The compound of claim 2, wherein $A^1$ is aryl optionally substituted with one or more of —$COR^8$.

4. The compound of claim 2, wherein $R^7$ is chloride.

5. The compound of claim 2, wherein $R^1$, $R^2$, $R^3$, and $R^5$ each represent independently for each occurrence H or alkyl.

6. The compound of claim 1, wherein said compound is one of the following:

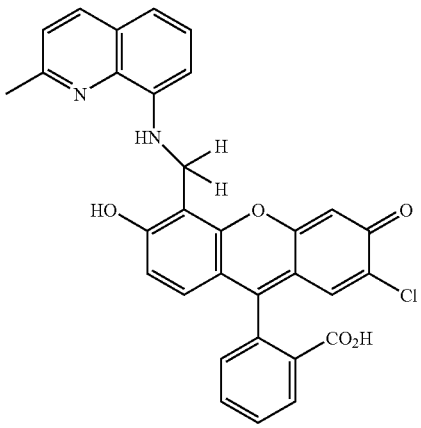

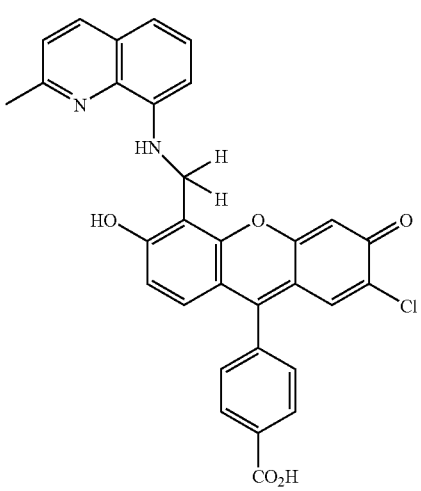

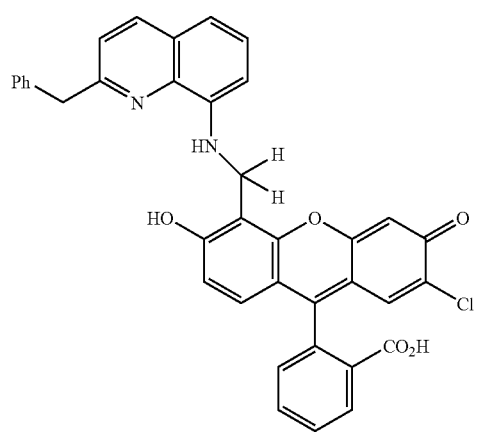

-continued
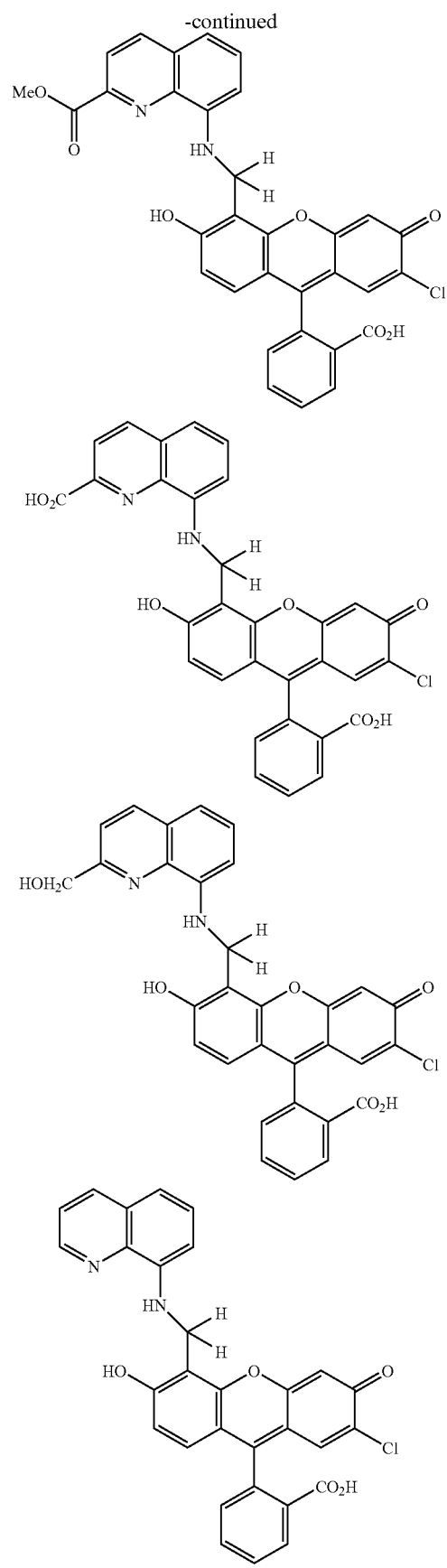
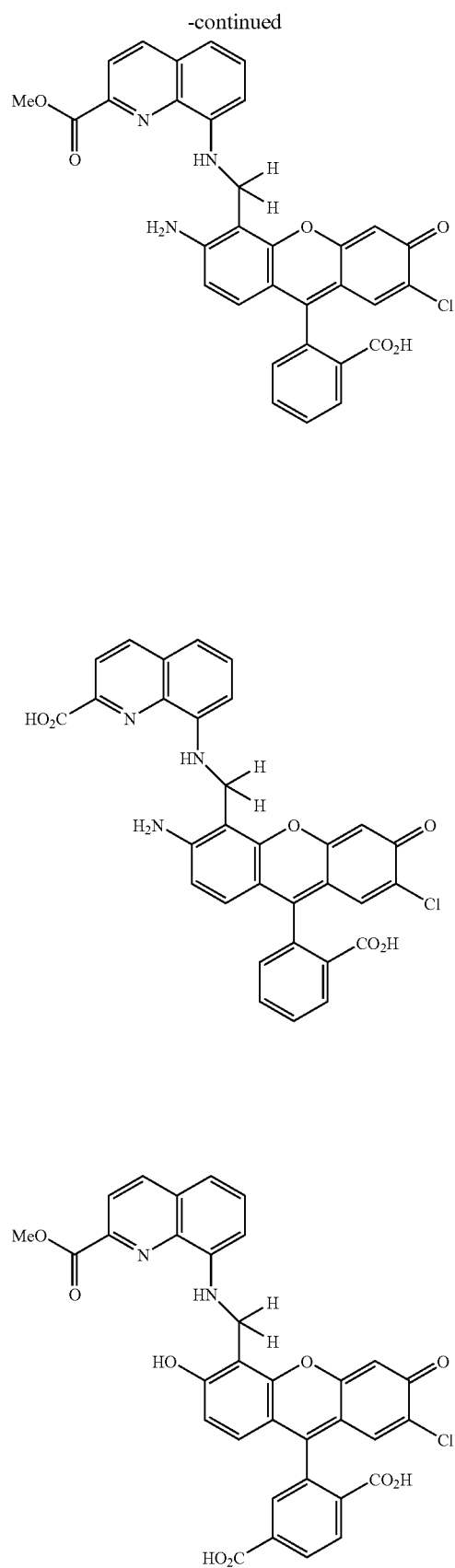

-continued
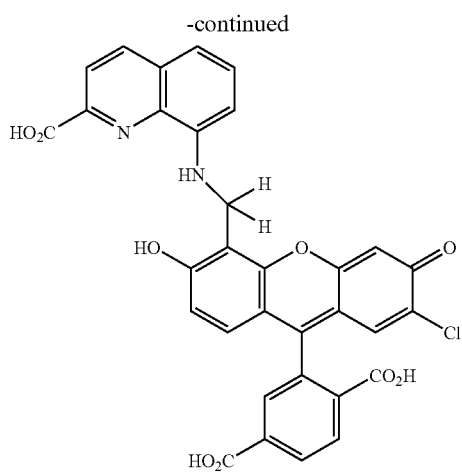
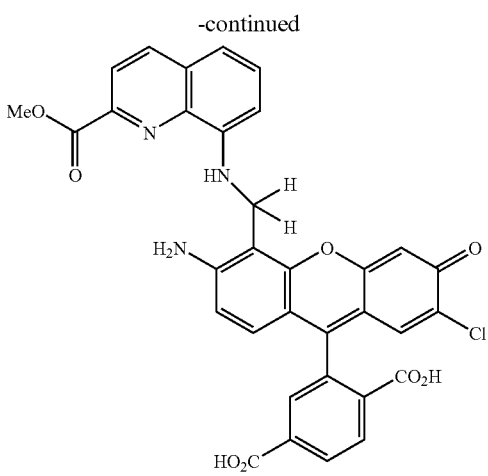
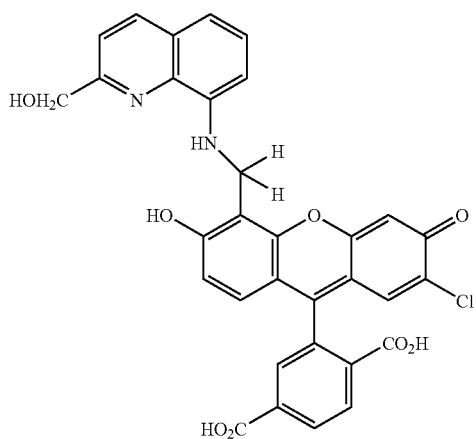
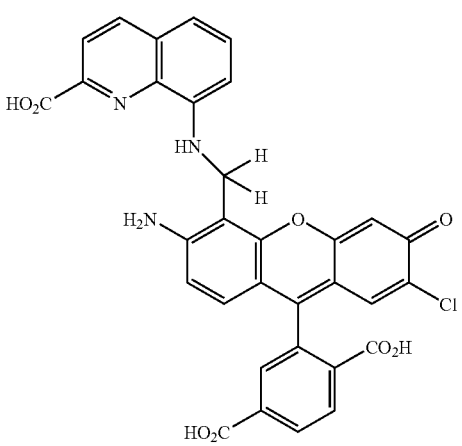
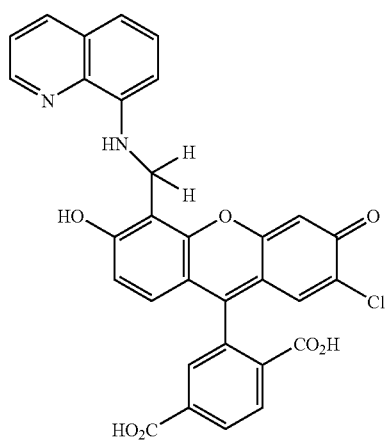
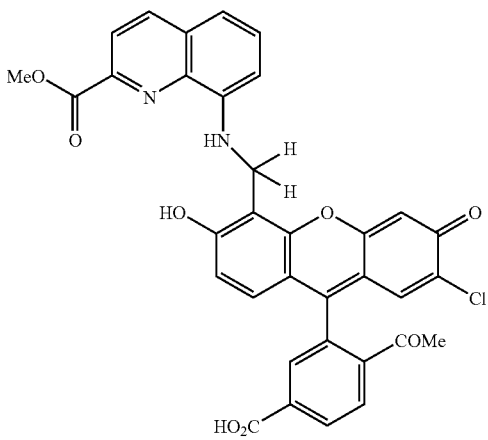

-continued
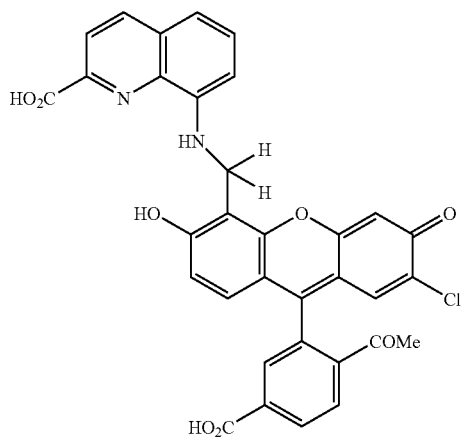
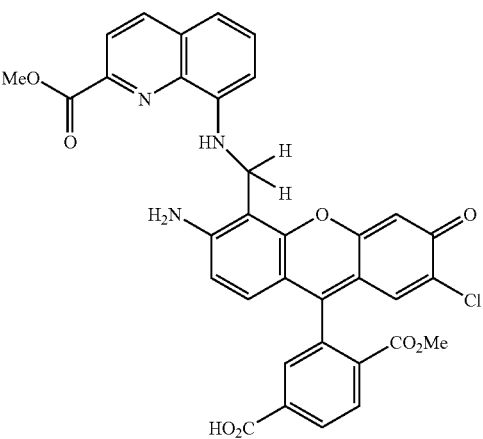
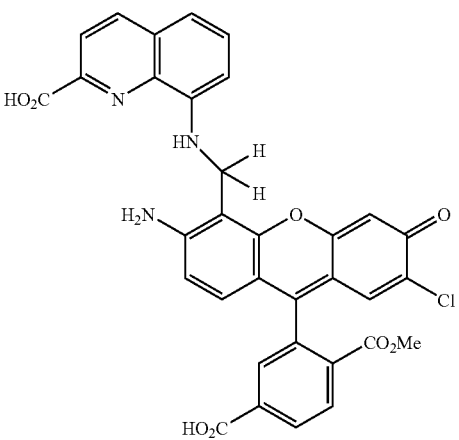
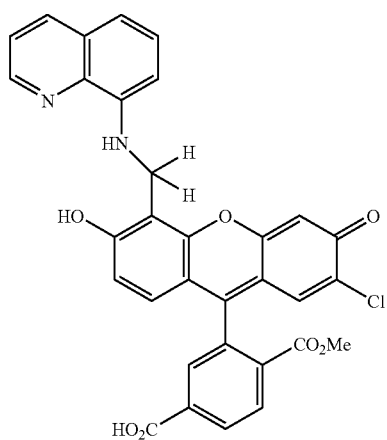
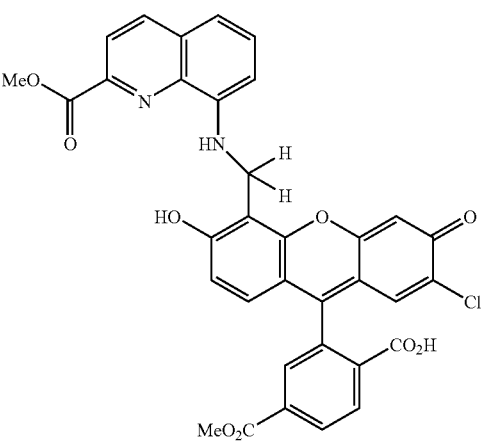

-continued
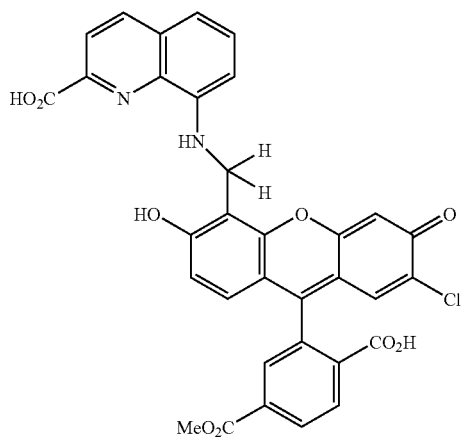
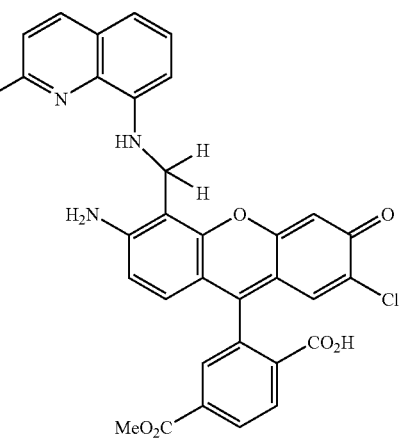
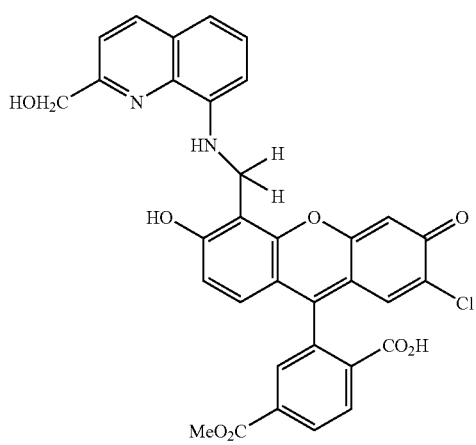
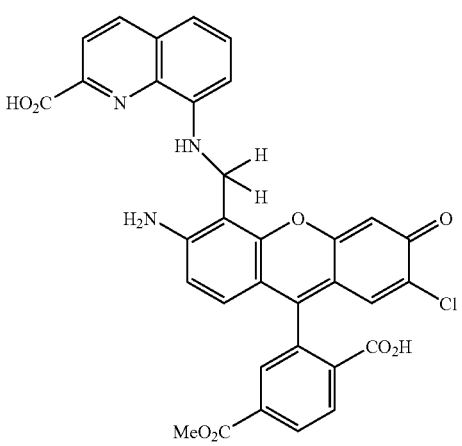
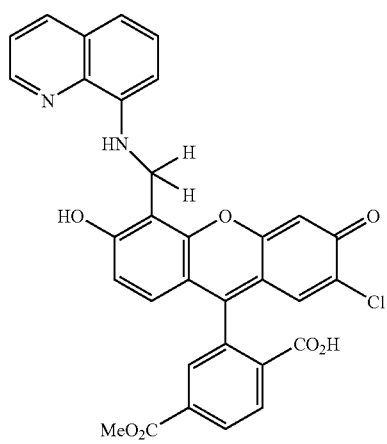
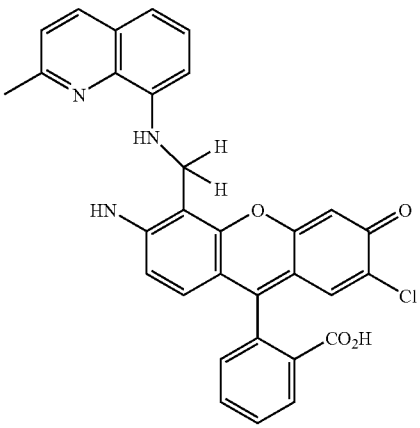

65
-continued
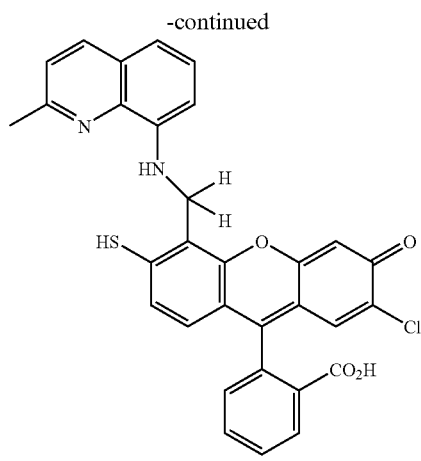
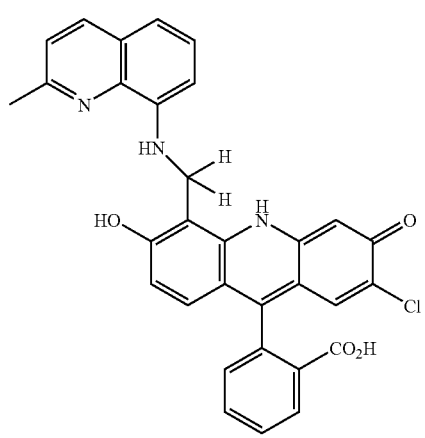
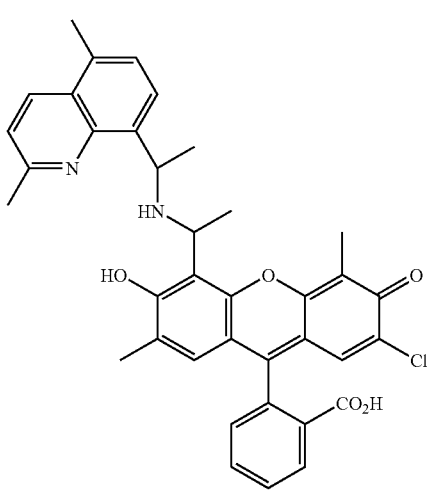
66
-continued
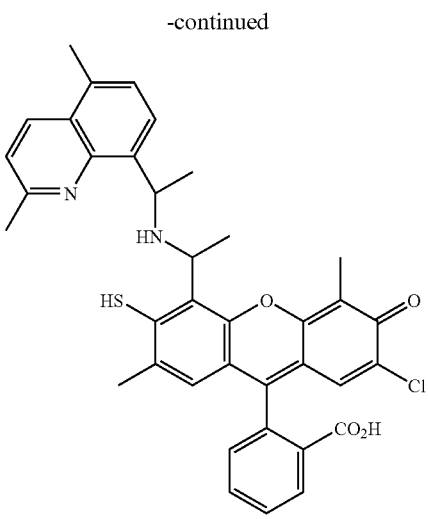
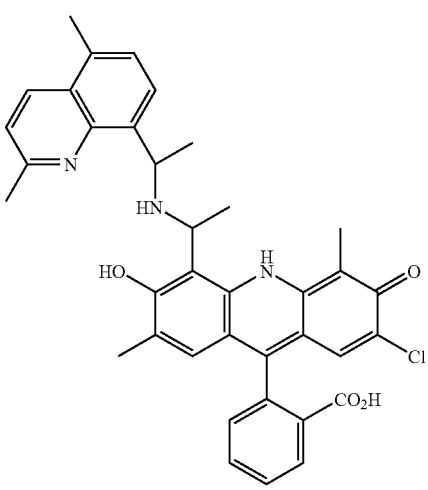
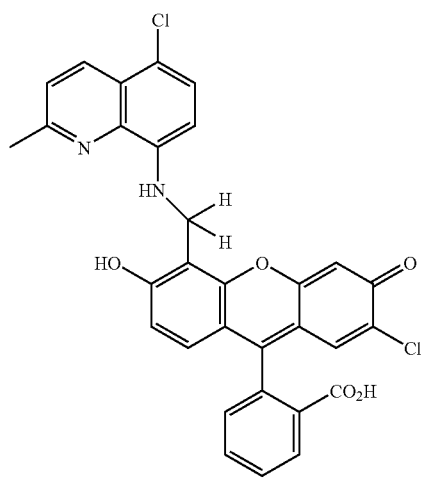

-continued
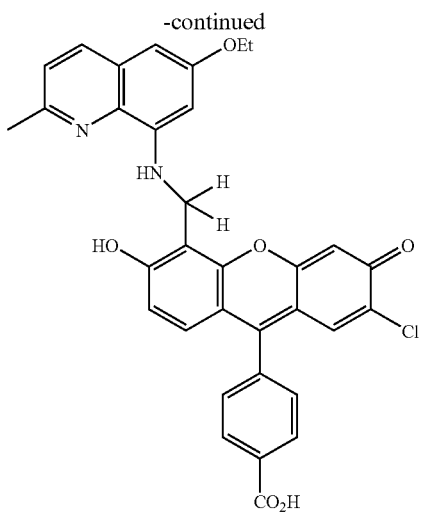
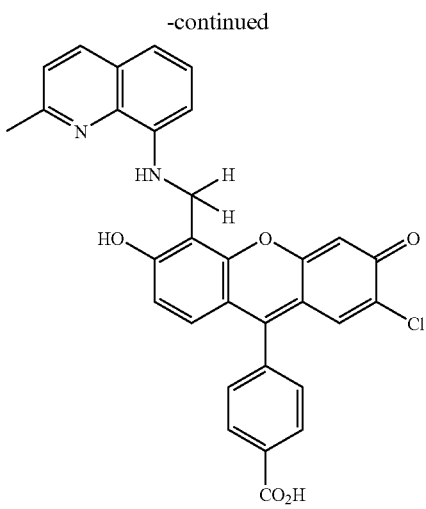
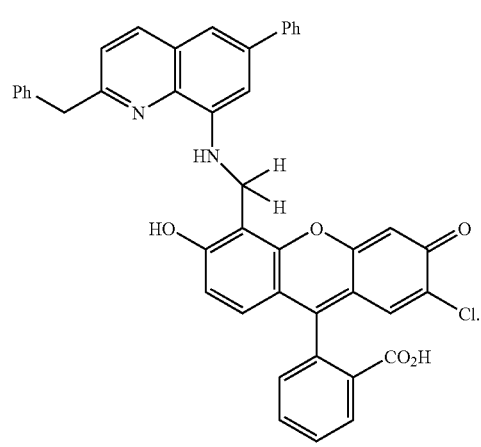
7. The compound of claim 1, wherein said compound is one of the following:
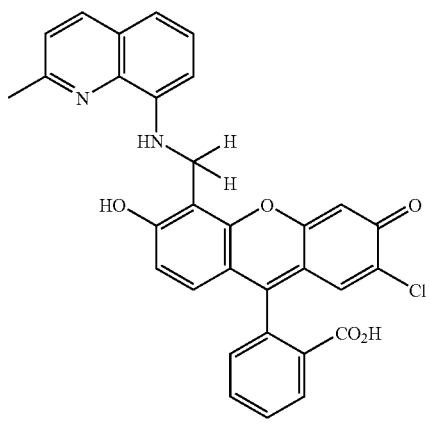
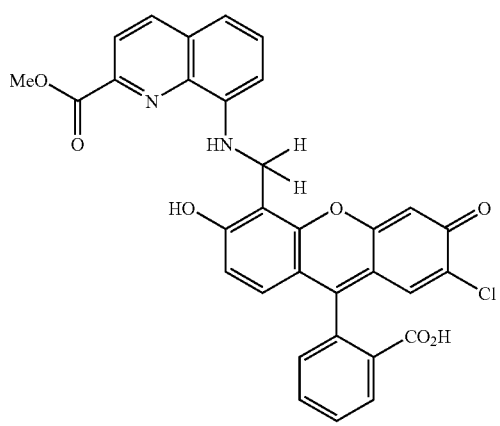

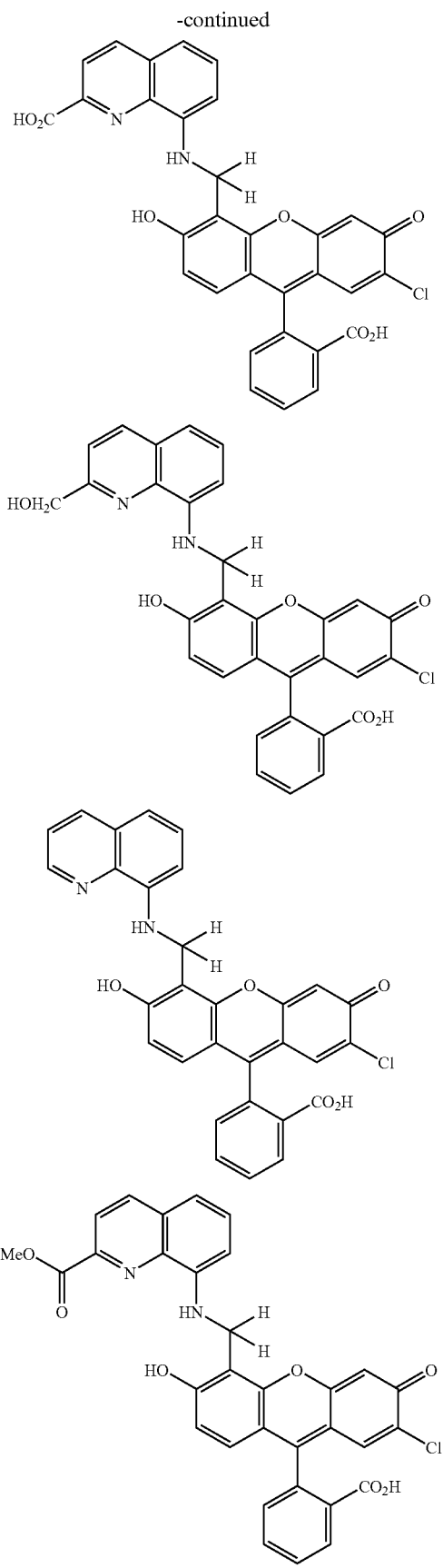
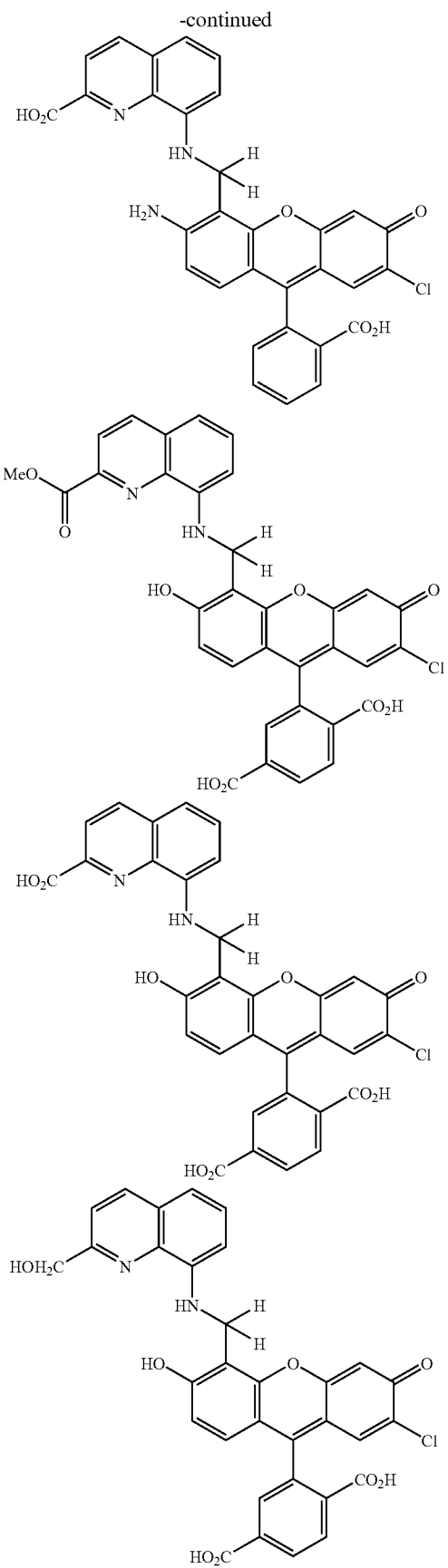

-continued

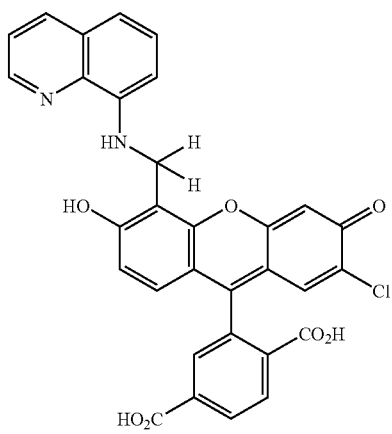

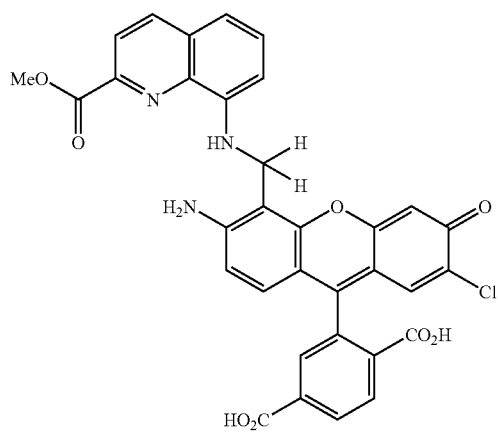

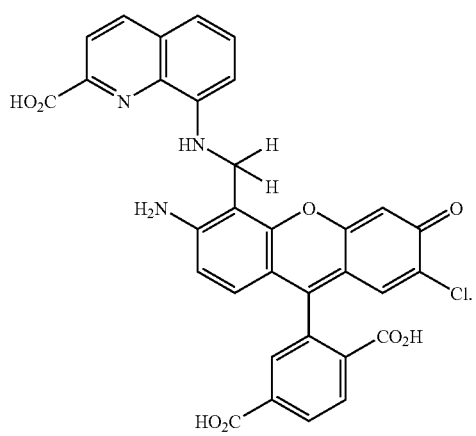

8. The compound of claim 1, wherein said compound is:

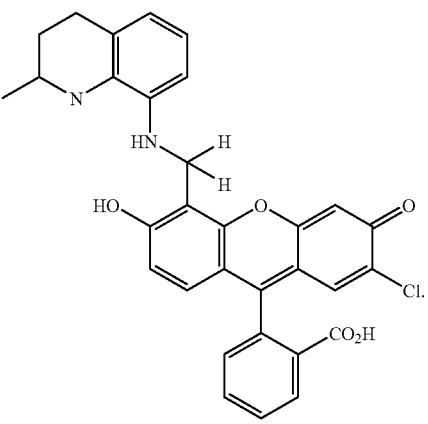

9. A compound represented by Formula II, comprising:

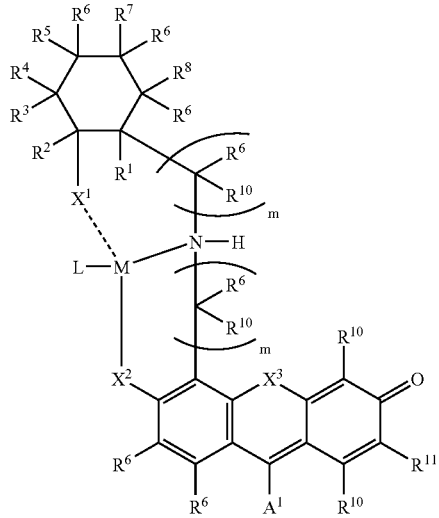

II wherein,
$A^1$ is aryl or heteroaryl, both of which are optionally substituted with one or more of halogen, alkoxyl, —OH, —N$(R^{12})_2$, —COR$^{12}$, —CO$_2$R$^{12}$, —N(R$^{12}$)C(O)R$^{12}$, or —C(O)N(R$^{12}$)$_2$;

L is a ligand;

M is a transition metal;

$X^1$ is —OR$^9$, —SR$^9$, —N=R$^9$, or —N(R$^{13}$)R$^9$;

$X^2$ is —O—, —S—, or —N(R$^{13}$)—;

$X^3$ is —O—, —S—, or —N(R$^{13}$)—;

$R^1$, $R^3$, $R^5$, $R^7$, $R^8$ and $R^{10}$ each represent independently for each occurrence H, alkyl, aryl or heteroaryl; or $R^1$ and $R^8$ taken together form a bond; or $R^5$ and $R^7$ taken together form a bond;

$R^2$, $R^4$, and $R^6$ each represent independently for each occurrence H, alkyl, aryl, heteroaryl, aralkyl, halogen, alkoxyl, —COR$^{12}$, or —CO$_2$R$^{12}$; or $R^2$ and $R^3$ taken together form a bond; or $R^4$ and $R^9$ taken together form a 5-6 member ring optionally substituted with one or more of alkyl, hydroxyalkyl, aryl, aralkyl, halogen, alkoxyl, —N(R$^9$)$_2$, —COR$^9$, —CO$_2$R$^9$, —N(R$^9$)C(O)R$^9$, or —C(O)N(R$^9$)$_2$;

$R^9$ is H, alkyl, aryl, heteroaryl, or aralkyl;

$R^{11}$ is H, alkyl, aryl, heteroaryl, aralkyl, or halogen;

$R^{12}$ represents independently for each occurrence H, alkyl, aryl, heteroaryl, or aralkyl;

$R^{13}$ represents independently for each occurrence H or $(C_1-C_6)$alkyl;

m represents independently for each occurrence 0, 1, 2, 3, or 4; and the stereochemical configuration at any stereocenter of a compound represented by II is R, S, or a mixture of these configurations.

10. The compound of claim 9, wherein said compound is represented by Formula IIa:

wherein, $A^1$ is aryl or heteroaryl, both of which are optionally substituted with one or more of halogen, alkoxyl, —OH, —N$(R^8)_2$, —COR$^8$, or —CO$_2$R$^8$;

L is a ligand;

M is a transition metal;

$X^1$ is —O—, —S—, or —N$(R^6)$—;

$X^2$ is —O—, —S—, or —N$(R^6)$—;

$R^1$ represents independently for each occurrence H, alkyl, hydroxyalkyl, aryl, aralkyl, halogen, alkoxyl, —N$(R^9)_2$, —COR$^9$, —CO$_2$R$^9$, —N$(R^9)$C(O)R$^9$, or —C(O)N$(R^9)_2$;

$R^2$, $R^3$, and $R^5$ each represent independently for each occurrence H, alkyl, halogen, alkoxyl, —COR$^8$, or —CO$_2$R$^8$;

$R^4$ and $R^6$ each represent independently for each occurrence H or alkyl;

$R^7$ is halogen;

$R^8$ represents independently for each occurrence H, alkyl, aryl, heteroaryl, or aralkyl;

m represents independently for each occurrence 0, 1, or 2;

the stereochemical configuration at any stereocenter of a compound represented by IIa is R, S, or a mixture of these configurations; and $R^1$ is optionally coordinated to M.

11. The compound of claim 10, wherein $A^1$ is aryl optionally substituted with one or more of —COR$^8$.

12. The compound of claim 10, wherein $R^1$, $R^2$, $R^3$, and $R^5$ each represent independently for each occurrence H or alkyl.

13. The compound of claim 10, wherein $R^7$ is chloride.

14. The compound of claim 10, wherein M is Cu, Co, Fe, Ni, Zn, Ru, or Rh.

15. The compound of claim 10, wherein M is Cu.

16. The compound of claim 10, wherein L is halogen, alkoxy, —OC(O)alkyl, —OC(O)aryl, or —OC(O)aralkyl.

17. The compound of claim 10, wherein L is halogen.

18. A method of detecting, and optionally quantifying the concentration of, an analyte in a sample, comprising:

a. Adding to a sample a compound;

b. Measuring the fluorescence of the sample; and c. Determining whether the analyte is present in the sample, and optionally the concentration of the analyte in the sample;

wherein the compound is represented by Formula I, comprising:

wherein $A^1$ is aryl or heteroaryl, both of which are optionally substituted with one or more of halogen, alkoxyl, —OH, —N$(R^{12})_2$, —COR$^{12}$, —CO$_2$R$^{12}$, —N$(R^{12})$C(O)R$^{12}$, or —C(O)N$(R^{12})_2$;

$X^1$ is —OR$^9$, —SR$^9$, —N=R$^9$, or —N$(R^{13})$R$^9$;

$X^2$ is —OR$^{13}$, —SR$^{13}$, or —N$(R^{13})_2$;

$X^3$ is —O—, —S—, or —N$(R^{13})$—;

$R^1$, $R^3$, $R^5$, $R^7$, $R^8$ and $R^{10}$ each represent independently for each occurrence H, alkyl, aryl or heteroaryl; or $R^1$ and $R^8$ taken together form a bond; or $R^5$ and $R^7$ taken together form a bond;

$R^2$, $R^4$, and $R^6$ each represent independently for each occurrence H, alkyl, aryl, heteroaryl, aralkyl, halogen, alkoxyl, —COR$^{12}$, or —CO$_2$R$^{12}$; or $R^2$ and $R^3$ taken together form a bond; or $R^4$ and $R^9$ taken together form a 5-6 member ring optionally substituted with one or more of alkyl, hydroxyalkyl, aryl, aralkyl, halogen, alkoxyl, —N$(R^9)_2$, —COR$^9$, —CO$_2$R$^9$, —N$(R^9)$C(O)R$^9$, or —C(ON$(R^9)_2$;

$R^9$ is H, alkyl, aryl, heteroaryl, or aralkyl;

$R^{11}$ is H, alkyl, aryl, heteroaryl, aralkyl, or halogen;

$R^{12}$ represents independently for each occurrence H, alkyl, aryl, heteroaryl, or aralkyl;

$R^{13}$ represents independently for each occurrence H or $(C_1-C_6)$alkyl;

m represents independently for each occurrence 0, 1, 2, 3, or 4; and the stereochemical configuration at any stereocenter of a compound represented by I is R, S, or a mixture of these configurations.

19. The method of claim 18, wherein the analyte is nitric oxide.

20. A kit for detecting an analyte, comprising a compound and instructions for using the composition to detect an analyte;

wherein the compound is represented by Formula I, comprising:

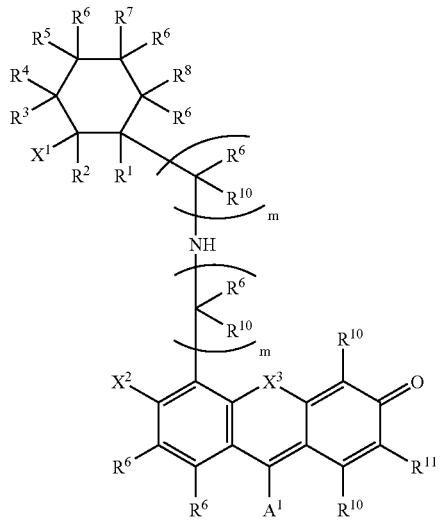

I wherein $A^1$ is aryl or heteroaryl, both of which are optionally substituted with one or more of halogen, alkoxyl, —OH, —N($R^{12}$)$_2$, —COR$^{12}$, —CO$_2$R$^{12}$, —N($R^{12}$)C(O)R$^{12}$, or —C(O)N($R^{12}$)$_2$;

$X^1$ is —OR$^9$, —SR$^9$, —N=R$^9$, or —N($R^{13}$)R$^9$;

$X^2$ is —OR$^{13}$, SR$^{13}$, or —N($R^{13}$)$_2$;

$X^3$ is —O—, —S—, or —N($R^{13}$)—;

$R^1, R^3, R^5, R^7, R^8$ and $R^{10}$ each represent independently for each occurrence H, alkyl, aryl or heteroaryl; or $R^1$ and $R^8$ taken together form a bond; or $R^5$ and $R^7$ taken together form a bond;

$R^2, R^4$, and $R^6$ each represent independently for each occurrence H, alkyl, aryl, heteroaryl, aralkyl, halogen, alkoxyl, —COR$^{12}$, or —CO$_2$R$^{12}$; or $R^2$ and $R^3$ taken together form a bond; or $R^4$ and $R^9$ taken together form a 5-6 member ring optionally substituted with one or more of alkyl, hydroxyalkyl, aryl, aralkyl, halogen, alkoxy, —N($R^9$)$_2$, —COR$^9$, —CO$_2$R$^9$, —N($R^9$)C(O)R$^9$, or —C(O)N($R^9$)$_2$;

$R^9$ is H, alkyl, aryl, heteroaryl, or aralkyl;

$R^{11}$ is H, alkyl, aryl, heteroaryl, aralkyl, or halogen;

$R^{12}$ represents independently for each occurrence H, alkyl, aryl, heteroaryl, or aralkyl;

$R^{13}$ represents independently for each occurrence H or ($C_1$-$C_6$)alkyl;

m represents independently for each occurrence 0, 1, 2, 3, or 4; and the stereochemical configuration at any stereocenter of a compound represented by I is R, S, or a mixture of these configurations.

* * * * *

UNITED STATES PATENT AND TRADEMARK OFFICE
CERTIFICATE OF CORRECTION

PATENT NO. : 7,494,821 B2
APPLICATION NO. : 11/498280
DATED : February 24, 2009
INVENTOR(S) : Lippard et al.

Page 1 of 1

It is certified that error appears in the above-identified patent and that said Letters Patent is hereby corrected as shown below:

In claim 8, column 72 at line 2, please replace

" 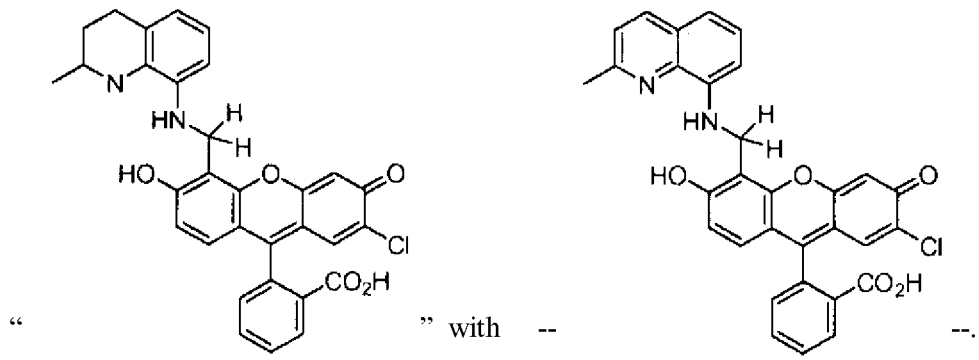 " with -- -- .

Signed and Sealed this

Twenty-first Day of April, 2009

JOHN DOLL
*Acting Director of the United States Patent and Trademark Office*